United States Patent [19]

Kelly et al.

[11] 4,256,898
[45] Mar. 17, 1981

[54] α(SUBSTITUTED) AMINO-3-SUBSTITUTED-2-ISOXAZOLINE-5-ACETIC ACIDS (ESTERS)

[75] Inventors: Robert C. Kelly; Wendell Wierenga, both of Kalamazoo, Mich.

[73] Assignee: The Upjohn Company, Kalamazoo, Mich.

[21] Appl. No.: 62,857

[22] Filed: Jul. 31, 1979

Related U.S. Application Data

[63] Continuation-in-part of Ser. No. 905,963, May 15, 1978, abandoned.

[51] Int. Cl.$^3$ ............................................. C07D 261/04
[52] U.S. Cl. ................................. 548/240; 548/243; 548/246
[58] Field of Search ........................ 548/240, 243, 246

[56] References Cited

U.S. PATENT DOCUMENTS

| | | | |
|---|---|---|---|
| 3,444,187 | 5/1969 | Ueyanagi et al. | 548/243 |
| 3,856,807 | 12/1974 | Hanka et al. | 548/240 |

FOREIGN PATENT DOCUMENTS 1154026  6/1969  United Kingdom ..................... 548/243

*Primary Examiner*—Anton H. Sutto
*Attorney, Agent, or Firm*—Sidney B. Williams, Jr.

[57] ABSTRACT

Chemical process for preparing AT–125 and its analogs and intermediates used in the process.

21 Claims, No Drawings

α(SUBSTITUTED)-AMINO-3-SUBSTITUTED-2-ISOXAZOLINE-5-ACETIC ACIDS (ESTERS)

CROSS REFERENCE TO RELATED CASES

This application is a continuation-in-part of application Ser. No. 905,963, filed May 15, 1978, now abandoned.

BACKGROUND OF THE INVENTION

1. Field of the Invention

The invention concerns a novel method for preparing ($\alpha$S,5S)-$\alpha$-amino-3-chloro-2-isoxazoline-5-acetic acid (AT-125) and novel analogs thereof. The invention also includes novel intermediates for making AT-125 and said analogs, novel compositions prepared from and methods of using AT-125 and said analogs.

2. Description of the Prior Art

The compound AT-125 and the microbiological process for producing it are claimed in U.S. Pat. Nos. 3,856,807 and 3,878,047, respectively. These patents also disclose the antitumor and antimicrobial activity of AT-125.

SUMMARY OF THE INVENTION

The novel compounds of this invention are selected from the group consisting of racemic mixtures and optically active isomers of compounds having the formula

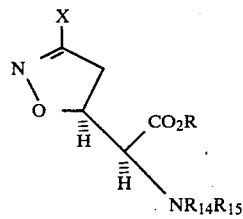

I wherein R is selected from the group consisting of hydrogen, alkyl of from 1 to 8 carbon atoms, inclusive, halogenated alkyl of from 1 to 3 halogen atoms, and 1 to 5 carbon atoms, inclusive, aralkyl of from 7 to 20 carbon atoms, inclusive; and substituted aralkyl of from 7 to 20 carbon atoms, inclusive. X is selected from the group consisting of bromine, chlorine, fluorine and iodine, $-OR_1$, $-SR_1$, and $-NR'R''$ wherein $R_1$ is selected from the group consisting of alkyl of from 1 to 12 carbon atoms, inclusive, aryl of from 6 to 20 carbon atoms, inclusive; aralkyl of from 7 to 20 carbon atoms; inclusive; R' and R" are the same or different and are selected from the group consisting of hydrogen and alkyl of from 1 to 8 carbon atoms; $R_{14}$ and $R_{15}$ are selected from the group consisting of hydrogen,

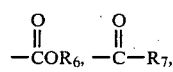

or when taken together with the nitrogen atom or the group

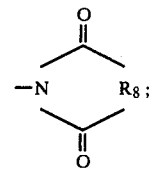

wherein $R_6$ is alkyl of from 1 to 8 carbon atoms, inclusive, halogenated alkyl of from 1 to 5 carbon atoms, inclusive, and 1 to 3 halogen atoms, inclusive, aralkyl of from 7 to 20 carbon atoms, inclusive, and substituted aralkyl of from 7 to 20 carbon atoms, inclusive, $R_7$ is selected from the group consisting of alkyl of from 1 to 12 carbon atoms, inclusive, aryl of from 6 to 20 carbon atoms, inclusive, aralkyl of from 7 to 20 carbon atoms, inclusive, and substituted aralkyl of from 7 to 20 carbon atoms, inclusive; and $R_8$ is selected from the group consisting of $$-\overset{R_9}{\underset{R_{10}}{C}}-\overset{R_{11}}{\underset{R_{12}}{C}}-$$

where $R_9$, $R_{10}$, $R_{11}$ and $R_{12}$ are selected from the group consisting of hydrogen and alkyl of from 1 to 5 carbon atoms, inclusive, (b)

$$\begin{array}{c}\phantom{x}\diagup CH_2 \diagdown\\ CH \phantom{xxx} CH_2\\ | \phantom{xxxxx} |\\ CH \phantom{xxx} CH_2\\ \diagdown CH_2 \diagup\end{array}$$

(c) orthointerphenylenes and (d) substituted orthointerphenylene with the proviso that when R, $R_{14}$ and $R_{15}$ are all hydrogen, X cannot be chlorine, and the further proviso that when $R_{14}$ and $R_{15}$ are both hydrogen and $R_8$ is orthointerphenylene, R can not be hydrogen or alkyl of from 1 to 8 carbon atoms.

In the foregoing designation of variables,

"Lower-alkyl" means methyl, ethyl, propyl, butyl, pentyl, hexyl, heptyl, octyl and the isomeric forms thereof.

Halogenated alkyl of from 1 to 5 carbon atoms, inclusive, and 1 to 3 carbon atoms, inclusive, means methyl, ethyl, propyl, butyl, pentyl and isomeric forms thereof substituted by 1 to 3 bromine, fluorine, chlorine or iodine atoms.

"Aryl" means phenyl and phenyl containing 1 to 3 substituents, the same or different and selected from the group consisting of halogen, alkoxy, alkyl and nitro.

"Aralkyl" means benzyl, phenethyl, phenpropyl, phenbutyl, phenpentyl, diphenylmethyl, three diphenyloctyl and isomeric forms thereof and fluorenylmethyl.

"Substituted aralkyl" means aralkyl in which the phenyl ring or rings contain 1 to 3 substituents, the same or different, and selected from the group consisting of halogen, alkoxy, alkyl and nitro. For example, p-methoxybenzyl, m-methoxybenzyl, p-nitrobenzyl, o-chlorobenzyl, 4-propyl-2-methylbenzyl, 2-chloro-4-methylbenzyl, 3,4-diethoxybenzyl, 3,4-diethoxybenzyl, 3,4,5-trichlorobenzyl and 3,4,5-trimethylbenzyl.

"Substituted orthointerphenlene" means lower-alkyl, lower-alkoxy, halogen, nitro, and cyano substituted orthointerphenylene. There can be combinations of substituents such as 4-propyl-2-methyl-, 2-chloro-4-methyl-, 3,4-diethoxy-, 3-cyano-4-ethoxy-phenyl and the like. The substituted phenyl is limited to a total of 10 carbon atoms.

Halogen means bromine, chlorine, fluorine and iodine.

This invention also pertains to a chemical process for preparing AT-125 and novel analogs thereof.

The process of this invention is advantageous in that it provides a complete chemical synthesis of AT-125, which heretofore, had only been prepared by a microbiological process. It involves preparing the compounds dl-trans-3-amino-4-hydroxy-cyclopentene which is in turn converted by a series of reactions to yield tricholomic acid derivatives, AT-125 and bromo, fluoro and iodo analogs thereof. These halo compounds are then converted to other analogs.

Tricholomic acid, first isolated by Takemoto et al, see Yakugaku Zasshi, 84, 1183 and 1230 (1964), is an amino acid having the structure

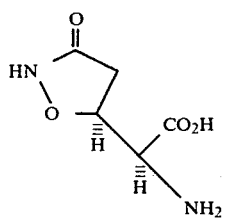

The compound is known to be flycidal and to have a taste that is appealing to man.

In addition to the Takemoto et al. work, other methods for the preparation of tricholomic acid have been described. They include [Iwasaki et al., Chem., Pharm. Bull. 17(5) 866–872 (1969)], [Iwasaki et al., Chem. Pharm. Bull 17(5) 873–878 (1969)], [Kamiya, T., Chem. Pharm. Bull. 17(5) 879–885 (1969)], [Kamiya, T., Chem. Pharm. Bull. 17(5) 886–889 (1969)], [Kamiya, T., Chem. Pharm. Bull. 17(5) 890–894 (1969)], [Kamiya, T., and Chem. Pharm. Bull. 17(5) 895–900 (1969)].

AT-125, or (α5,5S)-α-amino-3-chloro-α-isoxazoline-5-acetic acid, an antitumor and antimicrobial agent has the formula

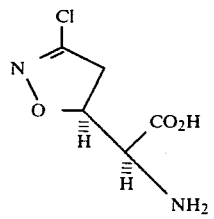

The novel process which proceeds through tricholomic acid and derivatives thereof, can be represented schematically as follows:

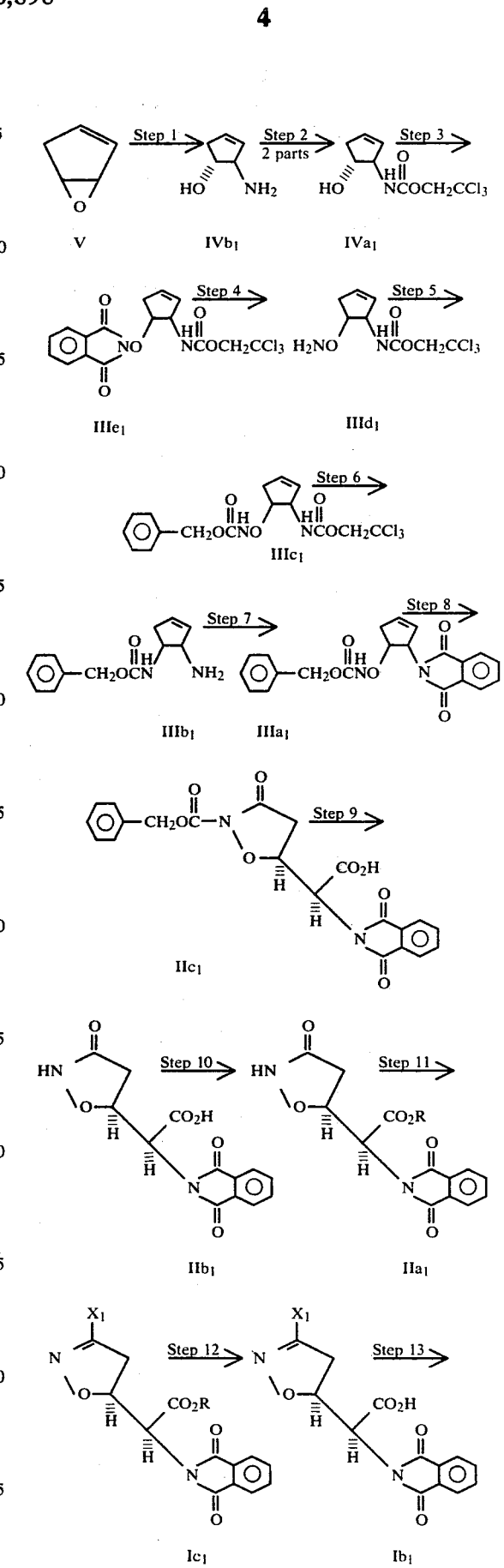

-continued $$\text{Ia}_1$$

(structure: oxazoline ring with X₁ substituent, bearing -CH₂-CH(NH₂)(CO₂H) side chain with stereochemistry indicated)

Another aspect of this invention is the use of novel intermediates in the process set forth above to prepare the compounds of formula I. These intermediates include (i) Compounds selected from the group consisting of racemic mixtures and optically active isomers of compounds having the formula II    VIId wherein R is selected from the group consisting of alkyl of from 1 to 12 carbon atoms, inclusive, halogenated alkyl of from 1 to 5 carbon atoms, inclusive, and 1 to 3 halogen atoms, inclusive, aryl of from 6 to 20 carbon atoms, inclusive, aralkyl of from 7 to 20 carbon atoms, inclusive, and substituted aralkyl of from 7 to 20 carbon atoms, inclusive; $R_{13}$ is selected from the group consisting of hydrogen alkoxycarbonyl, halogenated alkoxycarbonyl and aralkoxycarbonyl; $R_{14}$ and $R_{15}$ are selected from the group consisting of hydrogen, $$-COR_6, \quad -\overset{\overset{O}{\|}}{C}-R_7,$$

or when taken together with the nitrogen atom form the group $$-N\underset{\underset{O}{\|}}{\overset{\overset{O}{\|}}{\diagdown}}R_8$$

wherein $R_8$ is alkyl of from 1 to 8 carbon atoms, inclusive, halogenated alkyl of from 1 to 5 carbon atoms, inclusive, and 1 to 3 halogen atoms, inclusive, or alkyl of from 7 to 20 carbon atoms, inclusive, substituted aralkyl of from 7 to 20 carbon atoms, inclusive, substituted aralkyl of from 7 to 20 carbon atoms, inclusive, $R_7$ is selected from the group consisting of alkyl of from 1 to 8 carbon atoms, inclusive, aryl of from 6 to 20 carbon atoms, inclusive, aryl of from 6 to 20 carbon atoms, inclusive, aralkyl of from 7 to 20 carbon atoms, inclusive, substituted aralkyl of from 7 to 20 carbon atoms, inclusive, and $R_8$ is selected from the group consisting of $$\begin{array}{cc} R_9 & R_{11} \\ | & | \\ -C-\!\!\!-C- \\ | & | \\ R_{10} & R_{12} \end{array}$$

where $R_9$, $R_{10}$, $R_{11}$ and $R_{12}$ are selected from the group consisting of hydrogen and alkyl of from 1 to 5 carbon atoms, inclusive, $$\begin{array}{c} \diagdown \;\;\;CH_2 \\ CH \diagup \;\;\;\;\;\; \diagdown CH \\ | \;\;\;\;\;\;\;\;\;\;\;\; | \\ CH \;\;\;\;\;\;\;\;\; CH \\ \diagup \;\;\;\;\diagdown \;\;\;\diagup \\ CH_2 \end{array}$$

orthointerphenylene and substituted orthiointerphenylene, the proviso that other than when $R_{14}$ and $R_{15}$ form a ring with the nitrogen atom, one of $R_{14}$ and $R_{15}$ must always be hydrogen; when $R_{13}$, $R_{14}$, and $R_{15}$ are all hydrogen, R can not be hydrogen or alkyl of from 1 to 8 carbon atoms; and that when $R_{13}$ is aralkoxycarbonyl or halogenated alkoxy carbonyl, neither $$\underset{R_6OC-C}{\overset{\overset{O}{\|}}{}}$$

can be aralkoxycarbonyl or halogenated alkoxycarbonyl, nor $$\underset{R_7-C-}{\overset{\overset{O}{\|}}{}}$$

be aralkylcarbonyl or halogenated alkylcarbonyl;

(ii) Compounds selected from the group consisting of racemic mixtures and optically active isomers of compounds having the formula

IV (cyclopentene structure with $R_3O$ and $NR_4R_5$ substituents)

wherein $R_3$ is selected from the group consisting of hydrogen and $$\underset{\underset{O}{\|}}{\overset{\overset{O}{\|}}{RaS-}}$$

where Ra is alkyl of 1 to 8 carbon atoms and halogenated alkyl of 1 to 5 carbon atoms, inclusive, and 1 to 3 halogen atoms, inclusive, and aryl of from 6 to 20 carbon atoms, inclusive, and $R_4$ and $R_5$ are the same or different and are selected from the group consisting of hydrogen;

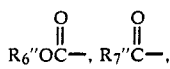

wherein, R''₆ and R''₇ are selected from the group consisting of alkyl of from 1 to 8 carbon atoms, inclusive, halogenated alkyl of from 1 to 5 carbon atoms, inclusive, and 1 to 3 halogen atoms, inclusive, aralkyl of from 7 to 20 carbon atoms, inclusive; substituted aralkyl of from 7 to 20 carbon atoms, inclusive, and when taken together with the nitrogen group

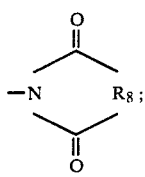

wherein R₈ is selected from (a) the group consisting of

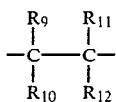

where R₉, R₁₀, R₁₁ and R₁₂ are selected from the group consisting of hydrogen and alkyl of from 1 to 5 carbon atoms, inclusive, (b)

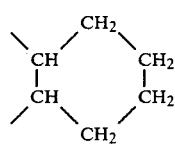

(c) orthointerphenylene and (d) substituted othointerphenylenes.

(iii) Compounds selected from the group consisting of racemic mixtures and optically active isomers of compounds having the formula

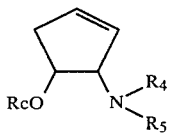      III wherein Rc is selected from the group consisting of amino; di-alkylamino,

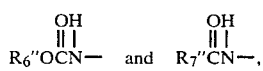

wherein R''₆ and R''₇ are selected from the group consisting of alkyl of from 1 to 8 carbon atoms, inclusive, halogenated alkyl of from 1 to 5 carbon atoms, inclusive, and 1 to 3 halogen atoms, inclusive, aralkyl of from 7 to 20 carbon atoms, inclusive, substituted aralkyl of from 7 to 20 carbon atoms, inclusive, and the group

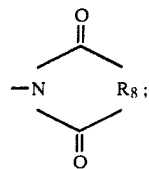

wherein R₈ is selected from (a) the group consisting of

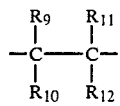

where R₉, R₁₀, R₁₁ and R₁₂ are selected from the group consisting of hydrogen and alkyl of from 1 to 5 carbon atoms, inclusive, (b)

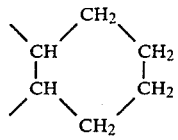

(c) orthointerphenylene and (d) substituted orthointerphenylene; R₄ and R₅ are the same or different and are selected from the group consisting of hydrogen, inclusive,

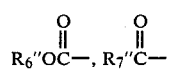

or when taken together with the nitrogen atom form the group

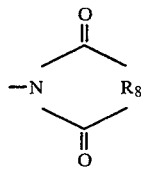

wherein R''₆, R''₇ and R₈ are the same as above; with the proviso that the groups R₃ and NR₄R₅ are never simultaneously the same.

The invention also pertains to compounds selected from the group consisting of racemic mixtures and optically active isomers of compounds having the formula

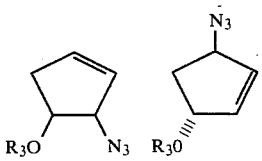

wherein R₃ is the same as above.

DETAILED DESCRIPTION OF INVENTION

AT-125 and novel derivatives thereof can be prepared in accordance with the process outlined above.

Step 1 is carried out in one of the three ways shown in the following schematic diagram:

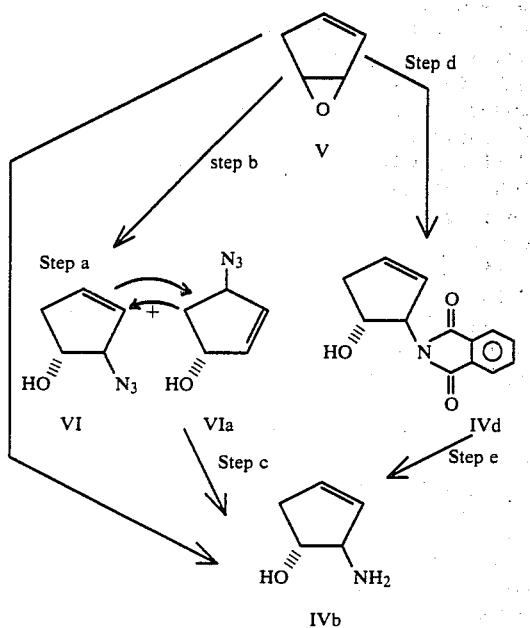

In the preferred route shown as Step a, epoxy cyclopentene V, available as described, for example, by Crandall et al., J. Org. Chem., 33:423 (1968), is reacted with a solution of ammonia in protic solvents such as water, methanol, ethanol or other alcohols or in non protic solvents such as diethyl ether, dimethyl formamide, tetrahydrofuran, or dimethoxy ethane. The reaction in the aprotic solvent is most efficaciously run in the presence of a catalyst such as dry, basic alumina as described for a similar reaction by Posner and Rogers, J. Amer. Chem. Soc., 99:8214 (1978). The reaction in protic solvents is generally run at −50° C. to +50° C. and at a concentration of epoxide from 0.01 M to 2 M. The molar ratio of ammonia to epoxide is generally from 1:1 to 50:1 most preferably in the range of 15:1 to 20:1. In non protic solvents the reaction is generally run at −20° to 100°. The concentration of epoxide in these solvents is generally 0.01 to 2 M and the mole ratio of ammonia to epoxide is generally 1:1 to 20:1, most preferably 1:1 to 5:1. The amine IVb so produced is generally isolated by evaporation of the excess ammonia and solvent and forming a crystalline salt of the crude residual amine. These salts may be formed using a solution of an acid such as toluenesulfonic acid, hydrochloric acid, hydrobromic acid, hydroiodic acid or other acids in a solvent such as water, methanol, ethanol, ether, 1,2-dimethoxy ethane, or p-dioxane. The salt is isolated by filtration and it crystallizes directly or by evaporation of the solvent followed by subsequent crystallization from a suitable solvent.

Alternatively, the crude amine IVb may be purified by adsorption on to a column of an acidic ion exchange resin such as Dowex 50W-X2(H+) or Amberlite 1R-120 (H+) followed by elution with a solvent such as water, methanol, ethanol, ether, tetrahydrofuran, 1,2-dimethoxy ethane or p-dioxane, containing a volative amine such as ammonia, methyl amine, diethyl amine or triethyl amine followed by evaporation of the volatile amine and solvent.

Similarly, the salts of hydroxy amine may be reconverted to the free amine by passing a solution of the salt in a solvent such as water, methanol, ethanol, tetrahydrofuran or 1,2-dimethoxy ethane through a basic ion exchange resin such as Dowex 1-X8 (OH−) or Amberlite 1RA-400 (OH−) and evaporating the eluate containing the amine.

The salts of amine IVb may also be reconverted to the free amine by treating an aqueous solution of the salts with a slight molar excess of a base such as sodium or potassium hydroxide saturating the resultant aqueous solution with a salt such as sodium chloride or sodium sulfate and subjecting the solution to constant solvent extraction with a solvent such as methylene chloride or chloroform. The amine IVb is then isolated by evaporating the solvent.

In a second route to amine IVb, as shown in the schematic diagram step b, the epoxide V is reacted with a mixture of hydrazoic acid and 1,1,3,3-tetramethyl guanidine in a solvent such as methylene chloride.

There are many references to the opening of epoxides with azide ion. See J. Org. Chem. 37, 1268 (1972); J. Am. Chem. Soc., 93, 1813 (1971); J. Org. Chem. 32, 1452 (1967); J. Med. Chem. 15, 175 (1972) and J. Am. Chem. Soc. 94, 7098 (1972). However, the high reactivity of the acyclic epoxide is unexpected. The use of 1,1,3,3-tetramethyl guanidine to solubilize azide ion in organic solvent has been described by Papa, J. Org. Chem. 31, 1426 (1966). However, the specific opening of epoxides to hydroxy azides with the reactants HN$_3$ and 1,1,3,3-tetramethyl guanidine in methylene chloride has not to applicants knowledge been reported before.

The molar ratios of hydrazoic acid and guanidine to epoxide should be from 1:1 to 5:1 and from 1:100 to 1:1 respectively. The reaction can be run at temperatures between about −50° to 100° at concentrations from 0.01 to 2 M. Under these conditions the dl-3,4-epoxycyclopentene is extremely reactive. Solvents other than methylene chloride that can be used include tetrahydrofuran, dimethylformamide p-dioxane and glyme. The azide VI can be removed from the reaction mixture by conventional separation techniques, i.e. filtration, extraction, chromatography and combinations thereof.

An alternative procedure for step b may be represented schematically as follows

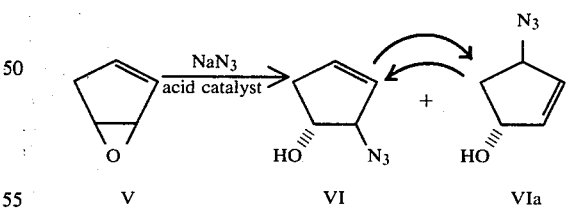

In this reaction dl-3,4-epoxycyclopentene is reacted with a mixture of sodium azide and a mild acid catalyst such as boric acid suspended in a solvent such as dimethylformamide, dimethylsulfoxide or acetonitrite. About 1 to 5 mole of sodium azide per mole of epoxide and 1 to 5 mole of boric acid per mole of epoxide is used. The reaction may be conducted between the temperatures of 0° and 125° for a period of about 1 hour to 10 days. The desired product DL-trans-3-azido-4-hydroxycyclopentane VI is recovered from the reaction mixture by conventional methods such as extraction and chromatography and combinations thereof.

On prolonged standing at room temperature and more rapidly on heating the azides VI and VIa each rearranges partially to the other azide. The two isomers VI and VIa may be separated chromatographically.

Step c involves the reduction of the dl-trans-3-azido-4-hydroxycyclopentene VI to dl-trans-3-amino-4-hydroxycyclopentene IVb. This type of reaction is well known in the art. However superior results are more likely to be obtained in polar solvents which dissolves the highly polar dl-trans-3-amino-4-hydroxycyclopentene. Suitable solvents include tetrahydrofuran, p-dioxane and 1,2-dimethoxyethane. The reaction can be conducted at temperatures of between −78° and 50° and concentration of 0.01 to 2 M. The amine IVb can be obtained from the reaction mixture by the methods described above for step a.

In the third route to IVb, step d, epoxide V is reacted with phthalimide in the presence of a catalyst such as potassium phthalimide or a tertiary amine in a solvent such as dimethylformamide, dimethylsulfoxide, tetrahydrofuran or acetonitrile. The molar ratios of phthalimide and catalyst to epoxide may be respectively, 1:1 to 10:1 and 1:10 to 1:1. The reaction may be run at 0° to 125° and for 1 hour to 20 days, the higher temperatures corresponding to shorter reaction times. The hydroxy phthalimide IVd can be obtained from the reaction mixture by convention separation techniques, i.e. extraction chromatography and combinations thereof.

In step e the phthalimide IVd is converted to the hydroxyamine IVb by treatment with hydrazine or hydroxylamine as is known in the art. Suitable solvents for this reaction include alcohols such as methanol and ethanol, tetrahydrofuran, dioxane, dimethylformamide, and acetonitrile. The molar ratio of phthalimide IVd to hydrazine or hydroxylamine is generally 1:1 to 1:10 and the reaction may be run at −20° C. to 100° C., most preferably at or near room temperature. The amino alcohol IVb may be isolated as obtained for step a above.

Step 2 involves reacting dl-trans-3-amino-4-hydroxycyclopentene IVb with trichloroethylchloroformate. In this step the amino group is blocked by the trichloroethoxycarbonyl group. The reaction is conducted by methods well known in the art for converting amines to urethanes. The reaction is conducted using a molar ratio of trichloroethylchloroformate to IVb of about 1:1 to 10:1 and at a temperature of about −20° to 50° C. for a period of about 20 minutes to 24 hours. The reaction is generally run in a solvent such as water, methanol, methylene chloride, tetrahydrofuran as p-dioxane containing a dissolved or suspended base such as sodium or potassium carbonate or a tertiary amine to capture the liberated acid. The reaction may also be run in a solvent which acts as its own base such as pyridine. The preferred solvent is water containing sodium carbonate. The urethane IVa can be recovered from the reaction mixture by conventional methods such as crystallization, filtration, distillation, extraction, chromatography and combinations thereof.

Other halo substituted alkyl halo formates can be used to block the amino group, i.e. iodoethylchloroformate. Also, the amino group can be blocked by an aralkoxycarbonyl group or an alkyloxycarbonyl group for example benzyloxycarbonyl and t-butyloxy carbonyl respectively. Methods for using these groups to block amines are well known in the art. For example background information on the preparation and removal of phthalimide, p-nitrobenzyl esters of carbobenzyloxy and carbo-tert-butyloxy derivatives of amino acids is described by R. A. Boissonas Chapter, "Selectively Removable Amino Protective Group used in the Synthesis of Peptides." In: Advances in Organic Chemistry, 3:159-190 (1963). Information on the use of the t-butyloxycarbonyl group to block amine is also described in ALDRICH Technical Information Bulletin entitled BOC-ON (September, 1976). Information on the use of trichloroethoxycarbonyl to block amines is disclosed by Windholz et al., Tetrahedron Letters, 2555 (1967). However the particular sequence used by the instant inventors have not to their knowledge been used before.

The urethanes IVa can also be prepared from salts of dl-trans-3-amino-4-hydroxycyclopentene formed by reacting the amine with protonic acids. The reaction is conducted by dissolving the salt in water and then treating the solution with sodium carbonate and trichloroformate or another blocking agent of the type described in step 2 above. The urethanes IVa again can be recovered from the mixture by conventional means.

Step 3 is conducted by reacting the urethane IVa with a slight molar excess of N-hydroxyhthalimide, diethyl azodicarboxylate and triphenylphosphine in a solvent. The reaction is conducted at a temperature of about −50° to 50°. Suitable solvents include tetrahydrofuran, ether, 1,2-dimethoxy ethane and p-dioxane. The preferred solvent is tetrahydrofuran. It should be noted that an inversion occurs during step 3 and that the urethane III$_e$ obtained is a cis isomer.

With slight modifications, other compounds, formed from the amine and other halo substituted alkyl halo formates, can be utilized in place of the dl-trans-3-amino-4-hydroxycyclopentene-N-trichloroethyl urethane in step 3.

Also compounds wherein the amino group is blocked by an aralkoxycarbonyl group can be used in step 3. For example,

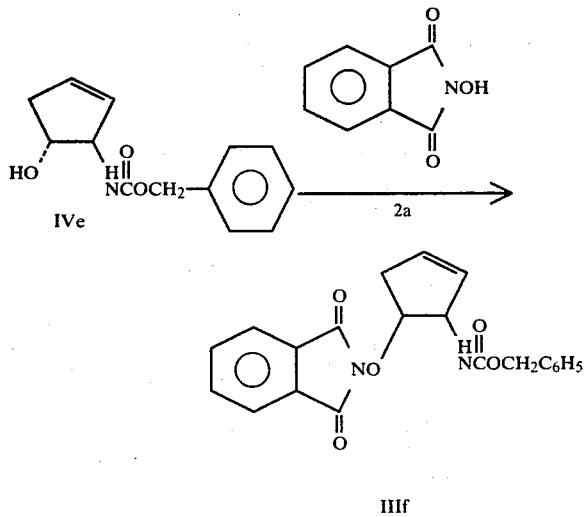

IIIf

The reaction and recovery procedure is essentially the same as in 3 above.

In step 4 the phthalimide compound III$_e$ is converted to the hydroxyl amine IIId by reacting it with a slight molar excess of hydrazine hydrate. This reaction is conducted in the presence of a solvent at a temperature of between −20° and 100° for a period of about 1 hour to 2 days. Solvents that can be used include tetrahydrofuran, ethanol, methanol, water, p-dioxane, and dimethylformamide. The hydroxyl amine IIId can be recovered from the reaction mixture by conventional means such as extraction, crystallization chromatography and combinations thereof.

In step 5 the hydroxylamine group of compound IIId is protected by reacting it with an alkoxychloroformate, haloalkoxychloroformate or an aralkoxyhaloformate such as benzyloxychloroformate to yield the carbamate IIIc. The reaction is conducted by using a molar ratio of aralkoxyhaloformate to IIIg of about 1:1 to 10:1 in a solvent such as tetrahydrofuran, 1,2-dimethoxy ethane, p-dioxane, acetonitrile or dimethylformamide containing a tertiary amine base such as triethyl amine or in a solvent such as pyridine which acts as its own base. The preferred solvent is pyridine. The reaction is generally run at a temperature of −20° to 50° C.

Conventional means such as crystallization, extraction, chromatography and combinations thereof can be used to recover the product from the reaction mixture.

In step 6, the amino group of the compound IIIc is deprotected by reacting it with zinc to yield the amino carbamate IIIb. This reaction may be conducted and worked up by several methods.

The preferred method involves conducting the reaction in the presence of methane sulfonic acid and methanol. The reaction is conducted at a temperature of between 0° C. and 50° C. for a period of about 30 minutes to 5 hours, using a molar ratio of zinc acid to IIIc of about 2:1 to 50:1.

In reaction 7 the amino carbamate IIIb is converted to its phthalimide IIIa by reacting it with 2-methoxy carbonylbenzoyl chloride and triethylamine in the presence of a solvent to yield phthalimide product IIIa. The reaction is conducted at a temperature of between −20° and 50° for a period of about 10 minutes to 5 hours using about 1:1 to 10:1 molar ratio of the benzoylchloride and 1:1 to 20:1 molar ratio of triethylamine to IIIc. Suitable solvents include tetrahydrofuran, ether, 1,2-dimethoxyethane, p-dioxane, dimethylformamide, and methylene chloride. The product IIIa is recovered from the reaction mixture by conventional means such as extraction, crystallization, chromatography and combinations thereof. The preferred method of recovery is extraction followed by chromatography or crystallization.

The starting material 2-methoxy carbonylbenzoyl chloride can be prepared by a method disclosed by Hoogwater et al., Recueil, 92, 819 (1973).

In step 8 the alkene phthalimide IIIa is reacted with a ruthenium compound such as ruthenium trichloride in the presence of an oxidizing agent such as potassium or sodium iodate and a solvent to yield the benzyloxycarbonyl derivative of tricholomic acid IIb. This reaction is conducted utilizing molar ratios of ruthenium chloride and sodium iodate to IIIa of about 1:1000 to 1:10 and 4:1 to 10:1 respectively, and at a temperature of about 0° to 50° for a period of about 20 minutes to 24 hours. Suitable solvents include water with acetone, methyl acetate, nitromethane, or t-butyl alcohol. The preferred solvent is acetone-water. The product IIb can be recovered from the reaction mixture by conventional means.

A product having the formula

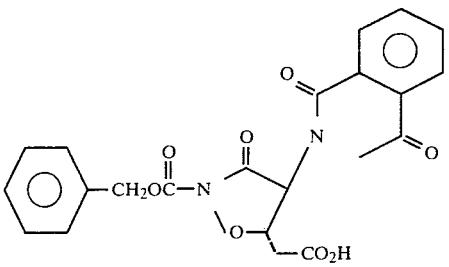

is also formed during reaction 8.

In step 9 the compound IIb is prepared by the deprotection of compound IIc. The particular conditions of the deprotection depends upon the particular oxycarbonyl groups, group ($R_{13}$) that is attached to nitrogen atom of the tricholomic acid ring. When that group is benzyloxy or aralkoxycarbonyl the deprotection can be conducted by dissolving the compound in a solvent and treating the solution with hydrogen in the presence of a conventional catalyst at a temperature of between 0° and 50° C. and atmospheric pressure for a period of about 20 minutes to 2 hours. Suitable solvents include ethyl acetate, ethanol, toluene and tetrahydrofuran. Suitable catalyst include palladium block, 5% palladium on carbon and palladium on barium carbonate. The product IIIa can be recovered by conventional means such as extraction, crystallization, chromatography and combinations thereof.

Alternatively, deprotection of compounds wherein $R_{13}$ is alkoxycarbonyl or aryloxycarbonyl can be conducted in the presence of an acid in solvents such as nitromethane and methylene chloride.

When $R_{13}$ is haloalkoxycarbonyl the deprotection is preferably conducted in the presence of zinc.

In step 10 the tricholomic acid derivative (IIb) is converted to ester IIa by methods for esterification well known in the art. For example the acid may be treated with diazo alkane or arylated diazomethane, for example diphenyl diazomethane or by treating IIa with a hindered tertiary amine such as N,N-diisopropyl-N-ethylamine followed by a benzyl halide such as diphenyl methyl chloride or p-methoxy benzyl bromide in a solvent such as tetrahydrofuran, ethyl acetate, acetonitrile or dimethylformamide.

In step 11 the tricholomic acid ester IIa is subjected to chlorination to yield the phthalimide-isoxozole acetic acid ester Ic. The preferred method of chlorition involves reacting II with hexamethylphosphorous triamide dichloride in the presence of a solvent. This reaction can be conducted at a temperature of between 25° and 60° for a period of about 24–72 hours. The molar ratios of hexamethylphosphorous triamide dichloride to IIa can be from 1 to 3. Wolkoff, CAN. J. CHEM. VOL. 53, p. 1333 (1975) discloses a process for converting benzoyl hydrogens into their corresponding hydrazonyl halides. However, attempts to convert trichloric acid, which contains an oxyamide group to its corresponding hydrazonyl halide compounds using this method were unsuccessful.

In step 12 the ester Ic is converted to Ib by either deesterification or deprotection of the amine. The preferred method is to perform deesterification first.

Deesterification of Ib involves reacting it with a hydrohalide gas in the presence of a solvent. The reaction is conducted at a temperature of about 5° to 30° for a period of about 1 through 4 hours. Suitable solvents include nitromethane, acetic acid and methylene chloride. The preferred solvent is nitromethane. The halogen moiety $X_1$ is dictated by the particular hydrogen halide used. For example, the use of hydrogen bromide, hydrogen chloride, hydrogen fluoride and hydrogen iodide yields compounds of formula Ib wherein $X_1$ is bromo, chloro, fluoro and iodo respectively.

The deprotection of the phthalimide amino acid produced by the deesterification of the ester Ic is accomplished by reacting the deesterification product with hydrazine hydrate in water or alcohol. The product ($\alpha$5,5S)-$\alpha$-amino-3-chloro-4,5-dihydro-5-isoxazole acetic acid or AT-125 (when $X_1$ is chloro) is recovered from the reaction mixture by conventional means such as extraction, crystallization, chromatography and combinations thereof.

Compounds of Formula Ia, Ia$_2$ and Ia$_3$ are prepared from compounds of formula Ia or IIa using conventional techniques for replacing halogen atoms with other moieties. For example:

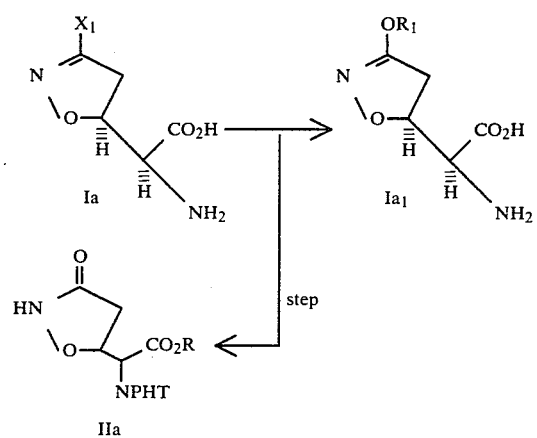

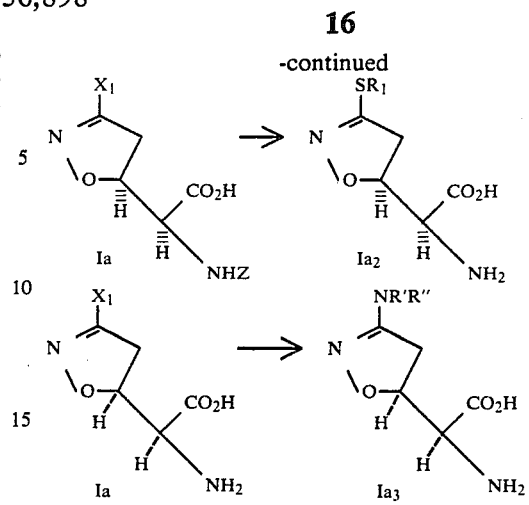

wherein $R_1$, $R'$, $R''$ and $X_1$ are the the same as defined above.

The reaction of Ia in methanol with one equivalent of sodium methoxide under an inert atmosphere at room temperature for 1–40 hours affords Ia wherein $R_1$=methyl. Alternatively, a suspension of Ia in an inert solvent such as dimethylformamide treated with an equivalent of an alkali metal salt of an alkyl or aryl mercaptan or primary or secondary aryl/aryl amine can be employed to afford analogous products Ia$_2$ and Ia$_3$, respectively.

The treatment of IIa with diazomethane in an ether solvent with a catalytic amount of boron trifluoride etherate gives Ia$_1$ with $R_1$=methyl.

The process of this invention requires the selective removal of various protecting groups in the presence of different protecting groups. In general, ease of removal of one group in the presence of another generally depends upon the particular reagents used. In this respect the protecting groups can be ranked in the order of least difficult to remove to most difficult to remove as shown in Table I.

| | Acid (H$^+$) | Hydrogen (H$_2$) | Zn (metal) | Hydrazine |
|---|---|---|---|---|
| 1. | Substituted aralkoxycarbonyl (i.e., p-methoxybenzyloxy carbonyl) | Substituted aralkoxycarbonyl | Halogenated alkoxycarbonyl | $-N\underset{O}{\overset{O}{\diamond}}R_8$ |
| 2. | Alkoxycarbonyl (i.e., t-butyloxycarbonyl) | Aralkoxycarbonyl | Substituted* aralkoxycarbonyl | |
| 3. | Aralkoxycarbonyl (i.e., benzyloxycarbonyl) | Alkoxycarbonyl* | alkoxycarbonyl* | |
| 4. | Halogenated-alkoxycarbonyl (i.e., trichloroethoxy carbonyl)* | Halogenated carbonyl* | | $-N\underset{O}{\overset{O}{\diamond}}R_8$ |
| 5. | $-N\underset{O}{\overset{O}{\diamond}}R_8$ * | | $-N\underset{O}{\overset{O}{\diamond}}R_8$ | |

*Generally cannot be removed without destroying total molecule.

Each step of the above process can either be conducted on racemic mixtures of the various reactants or a resolution can be conducted at any stage along the process and the remaining steps conducted upon optically active reactants.

The preferred method is to resolve the DL-trans-amino-4-hydroxy-cyclopentene IVb or a protonic acid salt thereof and then conduct the remainder of the process on the optically active isomers of the reactants.

Resolution of the racemic mixture can be accomplished, with modifications obvious to those skilled in the art, utilizing conventional methods of resolution. For example, the compound IVb may be resolved by forming salts with optically active acids such as D or L tartaric acid, the L-(+)-acid giving the antipode which leads to AT-125 of the natural configuration. The respective salts are obtained optically pure by recrystallization several times from a solvent such as ethanol. A particularly effective method of obtaining the optically pure isomer of IVb leading to natural AT-125 is to treat the racemic IVb in a solvent such as methanol first with deoxycholic acid which crystallizes out predominantly the antipode leading to enantiomeric AT-125. The mother liquors from this crystallization are then reconverted to the free amine by any of the methods described for step a above. This recovered amine now substantially enriched in the desired antipode is then brought to optical purity by formation and recrystallization of the L-tartaric acid salt.

Since the compounds I of this invention are amphoteric compounds, they form salts with acids, alkali metals (including ammonia), alkaline earth metals (including magnesium and aluminum), and amines. Metal salts can be prepared by dissolving them in water, and adding a dilute metal base until the pH of the solution is 7 to 8. Metal salts include the sodium, potassium and calcium salts. Amine salts, including those with organic bases such as primary, secondary, and tertiary, mono-, di-, and polyamines can also be formed using the above-described or other commonly employed procedures. Further, ammonium salts can be made, by well-known procedures. Other salts are obtained with therapeutically effective bases which impart additional therapeutic effects thereto. Such bases are, for example, the purine bases such as theophyllin, theobromin, caffein, or derivatives of such purine bases; antihistaminic bases which are capable of forming salts with weak acids; pyridine compounds such as nicotinic acid amide, isonicotinic acid hydrazide and the like; phenylalkylamines such as adrenalin, ephedrin, and the like; chloine, and others.

Acid salts can be made by neutralizing compounds of formula I with the appropriate acid to below about pH 7.0, and advantageously to about pH 2 to pH 6. Suitable acids for this purpose include hydrochloric, sulfuric, phosphoric, sulfamic, hydrobromic, and the like. Acid and base salts of the compounds can be used for the same biological purposes as the parent compound.

The compounds of formulas I and VIId inhibit the growth of microorganisms in various environments. For example, AT-125 is active against *Escherichia coli* and can be used to reduce, arrest, and eradicate slime production in papermill systems caused by its antibacterial action against this microorganism. AT-125 also can be used to prolong the life of cultures of *Trichomonas foetus, Trichomonas hominis,* and *Trichomonas vaginalis* by freeing them of *Escherichia coli* contamination. Further AT-125 can be used as the antifungal agent in the shoe uppers as disclosed in U.S. Pat. No. 3,130,505. Still, further, since AT-125 is active against *Bacillus subtilis* it can be used to minimize or prevent odor in fish or fish crates caused by this organism, or AT-125 can be used to swab laboratory benches and equipment in a mycological laboratory.

The compounds of formula I are also effective for treating bacterial infections and tumors in mammals, including humans.

The compositions of the present invention are presented for administration to humans and animals in unit dosage forms, such as tablets, capsules, pills, powders, granules, sterile parenteral solutions or suspensions, eye drops, oral solutions or suspensions, and water-in-oil emulsions containing suitable quantities of the compound of Formula I.

For oral administration, either solid or fluid unit dosage forms can be prepared. For preparing solid compositions such as tablets, the compound of FIG. 1 is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The watersoluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1 to 2.5 Gm.

The term "unit dosage form", as used in the specification, refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, dropperfuls, ampoules, vials, aerosols with metered discharges, segregated multiples of any of the foregoing, and other forms as herein described.

An effective quantity of the compound is employed in treatment. The dosage of the compound for treatment depends on many factors that are well known to those skilled in the art. They include for example, the route of administration and the potency of the particular compound. A dosage schedule for humans of from about 2 to about 200 mg. of compound in a single dose, administered parenterally or in the compositions of this invention, are effective for treating tumors and bacterial infections. More specifically, the single dose is from about 5 mg. to about 50 mg. of compound. The oral and rectal dose is from about 5 mg. to about 500 mg. in a single dose. More specifically, the single dose is from about 10 mg. to about 100 mg. of compound.

The following described preparations of AT-125 and analogs thereof are indicative of the scope of this invention and are not to be construed as limitative. Those skilled in the art will promptly recognize variations from the procedure both to the AT-125 and analog precursors as well as reaction conditions and techniques.

PREPARATION OF RACEMIC MIXTURES

Preparation 1 dl-3,4-Epoxycyclopentene

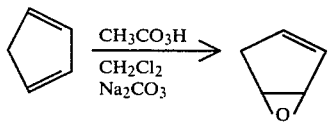

A 45 g. (0.68 M) quantity of cyclopentadiene is dissolved in 750 ml. of methylene chloride to which is added 290 g. of anhydrous sodium carbonate. The vigorously stirred mixture is treated dropwise over 40 min. with 110 ml. of 6.3 M peracetic acid (to which 1 g. of sodium acetate is added to neutralize possible traces sulfuric acid while holding the temperature below 20° in an ice bath. The reaction is then stirred an additional 3 hours at 20°–25°. The reaction is then filtered and 1–2 g. of sodium carbonate is added to the filtrate. The filtrate is distilled starting at 35 mm of pressure and ending at 20 mm with a distilling temperature ~30° (pot temperature never above 40°–45°) to yield 21.8 g. of dl-3,4-epoxycyclopentene.

NMR (CDCl$_3$, δ): 2.1–2.7 (m, 2H), 3.6–4.1 (m, 2H), 5.7–6.3 (m, 2H).

Preparation 2 dl-Trans-azido-4-hydroxycyclopentene (a)

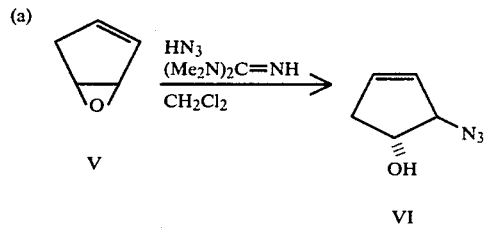

A 90 g. (1.38 M) quantity of sodium azide was added to 90 ml. of H$_2$O and 300 ml. of methylene chloride. The mixture is vigorously stirred, cooled to <10° and treated with 19 ml. of sulfuric acid. After 30 min. the methylene chloride layer is decanted and dried over sodium sulfate. The solution is then treated with 8 g. (0.07 M) of 1,1,3,3-tetramethylguamidine dissolved in 30 ml. of methylene chloride. The resultant solution is treated with the crude methylene chloride solution of 3,4-epoxycyclopentene prepared from 0.68 M of cyclopendadiene. After two and one half hours the solvent is evaporated in vacuo to yield DL-trans-azido-4-hydroxycyclopentene.

Preparation 2a dl-trans-azido-4-hydroxycyclopentene and dl-trans-azido-2-hydroxycyclopentene

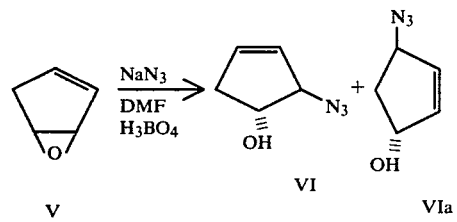

In an alternate procedure the crude methylene chloride solution of DL-3,4-epoxycyclopentene prepared from 36.6 mm of cyclopentadiene is concentrated under ~50 mm and <20°. The residue is added to a mixture of 8 g. (123 mM) of sodium azide and 8 g. (129 mM) of Boric Acid suspended in 200 ml. of dry dimethylformamide. The mixture is stirred at 25° for 17 hours. The reaction is then partitioned between water and ethyl acetate. The ethyl acetate layer is washed with water, dried over magnesium sulfate and evaporated in vacuum at 25°. The crude residue is combined with that from a previous 10 mM run and chromatographed over 2 linearly connected E. Merck size B columns of silica gel 60. The columns are eluted with (40–60) ethyl acetate-Skellysolve B and 30 ml. fractions were collected. Fractions 10–13 are collected and evaporated to yield left 2.64 g of dl-trans-azido-4-hydroxycyclopentene as a pale yellow oil. The overall yield from cyclopentadiene is 45%.

On standing dl-trans-azido-4-hydroxycyclopentene rearranges partially to dl-trans-azido-2-hydroxycyclopentene.

The two isomers are separated by chromatography over 2 linearly connected E. Merck size B columns of silica gel 60. The columns are eluted with (40-60) ethyl acetate-Skellysolve B and 30 ml. fractions are collected.

dl-Trans-3-amino-4-hydroxy-cyclopentene

NMR (CDCl₃, δ): 1.95-3.05 (m, CH₂), 3.5 (OH), 4.0-4.5 (m, CHOH,CHN₃), 5.6-6.2 (m, CH=CH).

IR (film, cm⁻¹): 3300 (OH), 2090 (azide).

dl-Trans-3-amino-2-hydroxy-cyclopentene

NMR (CDCl₃, δ): 1.9-2.2 (m, CH₂), 3.85-4.2 (OH), 4.25-4.7 and 4.7-5.1 (m, CHOH, CHN₃), 5.75-6.2 (m, CH=CH).

IR (film, cm⁻¹): 3300 (OH), 2090 (azide).

TLC (silica gel 60): Rf of isomer IVc is 0.60 and the Rf of isomer VI is 0.39 in (40-60) ethyl acetate-Skellysolve B.

Preparation 3
dl-trans-3-amino-4-hydroxy-cyclopentene

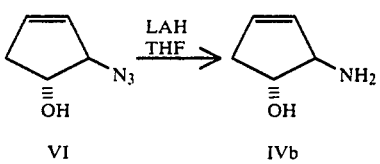

(a) A 2.2 g (57.9 mM) quantity of lithium aluminum-hydride is added to 90 ml. of ether and the stirred suspension cooled in an ice bath. To the above suspension is added 3.62 g. of pure DL-trans-azido-4-hydroxycyclopentene dissolved in 5 ml. of ether over 15 min. (exothermic with vigorous gas evolution). After stirring 2 hours, the reaction is cautiously treated with 2.2 ml. of water, 2.2 ml. of 15% sodium hydroxide and 2.2 ml. of water (initially, very exothermic with much gas evolution). After stirring an additional 15 min. the solids are removed by filtration. The filtrate is evaporated in vacuo leaving 1.96 g. of dl-trans-3-amino-4-hydroxycyclopentene, 5 which solidified to a low melting solid on standing. This material is extremely water soluble.

NMR (CDCl₃, δ): 1.8-2.9 (m, CH₂), 3.2 (OH, NH₂), 3.5-4.2 (m, CHOH, CHNH₂), 5.4-5.9 (m, CH=CH).

TLC (silica gel 60): Rf=0.24 in (1-20-80) conc. NH₄OH—MeOH—CH₂Cl₂.

(b) The total crude dl-trans-azido-4-hydroxycyclopentene from a 0.68 M scale 1,1,3,3-tetramethylguanidine assisted azide formation (Preparation 2a) is dissolved in 100 ml of tetrahydrofuran and the solution added over 30 minutes to a suspension of 25.8 g (0.68 M) of lithium aluminum hydride in 1 l. of tetrahydrofuran. The temperature of the reaction is maintained below 5° with a brine-ice bath during the addition. The reaction is then allowed to warm to 25° C. and stirred for 18 hours. The reaction is then recooled to 0° and treated successively with 25 ml. of water (exothermic and vigorous gas evolution), 25 ml. of 15% sodium hydroxide, and 25 ml. of water. After stirring for an additional one half hour, the mixture is filtered. The solids are washed with tetrahydrofuran. The combined filtrate and washings are evaporated in vacuo leaving 47.8 g. of crude dl-trans-3-amino-4-hydroxycyclopentene.

Preparation 4
dl-Trans-3-amino-4-hydroxycyclopentene toluenesulfonate salt

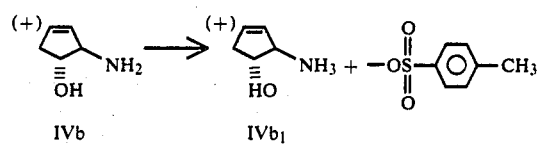

A 22.17 g. quantity of crude dl-trans-3-amino-4-hydroxy-cyclopentene dissolved in ~200 ml. of tetrahydrofuran and the solution treated with a saturated tetrahydrofuran solution containing 40 g. (0.21 M) of p-toluenesulfonic acid monohydrate. Crystals form rapidly. They are removed by filtration after a few minutes giving 14.5 g. of dl-trans-3-amino-4-hydroxycyclopentene toluenesulfonate salt m.p. 180°-182°. The mother liquors are concentrated and cooled giving another 18.9 g. of dl-trans-3-amino-4-hydroxycyclopentene toluenesulfonate as crystals m.p. 177°-181° for a total yield of 33.4 g.

Preparation 5 Preparation of
dl-3-Amino-4-hydroxycyclopentene from its toluenesulfate salt.

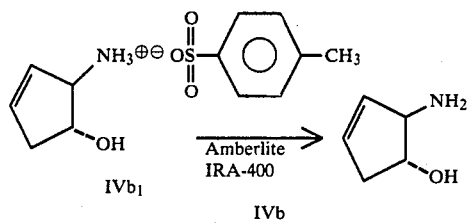

A 150 ml quantity of amberlite IRA-400 resin in its chloride form is washed on a fritted glass funnel successively with 6×150 ml of N sodium hydroxide, 3×150 ml of water and 3×150 ml of methanol. The beads are then slurry packed in a chromatography column containing methanol. A 10.95 g (40.4 mM) quantity of dl-trans-3-amino-4-hydroxycyclopentene toluenesulfonate dissolved in a minimum amount of methanol is then added to the top of the column and the column eluted with 750 ml of methanol. Evaporation of the total eluate gives 4.2 g. of an oil which solidifies on standing overnight under vacuum to give dl-3-amino-4-hydroxycyclopentene, m.p. 47°-50° C.

NMR (CDCl₃, δ): 1.8-2.9 (m, CH₂), 3.2 (OH, NH₂), 3.5-4.2 (m, CHOH, CHNH₂), 5.4-5.9 (m, CH=CH).

TLC (silica gel 60); Rf-0.24 in (1-20-80) conc. NH₄OH—MeOH—CH₂Cl₂. Detected by KMnO₄ spray reagent.

Preparation 5a
dl-Trans-3-amino-4-hydroxycyclopentene (IVb) and its p-toluenesulfonate salt

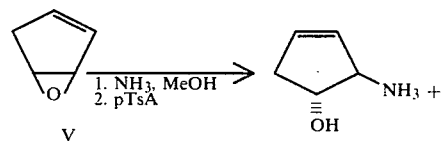

-continued

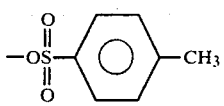

A 40 ml. quantity of dry methanol is cooled in an ice bath and ammonia gas bubbled to produce a saturated solution. To this ammonia solution is added 500 mg. of cyclopentene epoxide. The reaction is held at 0° for 24 hours and at 25° for 64 hours. The reaction is then concentrated in vacuo and the residue treated with 5 to 10 ml of tetrahydrofuran. The insoluble material is removed by centrifugation leaving a solution of hydroxy amine IVb. This is treated in a saturated solution of p-toluenesulfonic acid in tetrahydrofuran until the solution containing the amine becomes acidic. The voluminous crystalline precipitate is collected by filtration and dried. There is obtained 680 mg. of dl-trans-3-amino-4-hydroxycyclopentene toluenesulfonate salt.

Preparation 5b
dl-Trans-3-amino-4-hydroxycyclopentene IVb and its p-toluenesulfonate salt

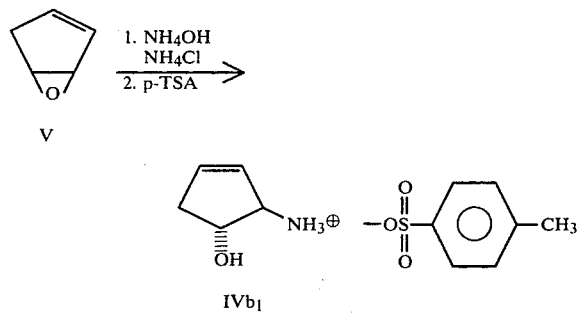

A 1.97 g. (24 mM) quantity of distilled epoxycyclopentene is added to an ice cold solution of 1.97 g. (39.4 mM) ammonium chloride in 20 ml. of conc. ammonium hydroxide. After stirring one half hour the reaction is warmed to 25° and stirred an additional 18 hours. The reaction is then extracted with ether to remove more polar impurities. The aqueous layer is saturated with sodium chloride subjected to continuous extraction with methylene chloride. The methylene chloride is dried over sodium sulfate and concentrated in vacuo leaving 1.15 g. of dl-trans-3-amino-4-hydroxycyclopentene which is treated with 1.54 g. (8.1 mM) of toluene sulfonic acid dissolved in tetrahydrofuran to yield 1.47 g. of dl-trans-3-amino-4-hydroxycyclopentene toluenesulfonate.

Utilizing a procedure similar to Preparation 5a but substituting the appropriate protonic acid for toluenesulfonic acid there is obtained racemic mixtures of di-p-tolyl-L-tartaric acid salt, m.p. 185°–190° (dec).
di-benzoyl-L-tartaric acid salt, m.p. 181°–183° (dec).
l-mandelic acid salt, m.p. 116°–117°. 2-pyrrolidone-5-carboxylic acid salt, m.p. 164°–172°.

Preparation 6
dl-Trans-4-hydroxy-3-phthalimidocyclopentene

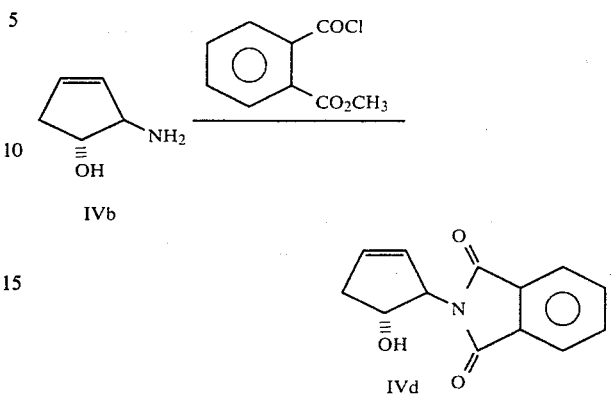

A quantity of dl-trans-4-hydroxy-3-amino-cyclopentene is dissolved in 450 ml of tetrahydrofuran and 87 ml. (0.60 M) of triethylamine. The solution is cooled to 0° and treated dropwise with 59.6 g. (0.3 M) of o-methoxy-carbonylbenzoylchloride over 50 min. The reaction is then allowed to warm to 25°. After 66 hours the reaction is partitioned between ethyl acetate and water. The ethyl acetate layer is dried over magnesium sulfate and distilled in vacuo to yield 62.4 g. of residual oil. This is chromatographed over 3 kg. of silica gel 60 eluted with 6 l. of (10–90), 2.5 l. of (15–85), and 11 l. of (20–80) acetonemethylene chloride. Two hundred fifty ml. fractions are collected. The product is found in fractions 38–61. These fractions crystallized on standing to yield 25.9 g. of dl-trans-4-hydroxy-3-phthalidocyclopentene.

A method for preparing O-methoxy-carbonylbenzoylchloride is described by Hoogwater et al., Rec. Trav. Chim. Pays-Bas, 92 (1973).

Preparation 6a
dl-Trans-4-hydroxy-3-phthalimido-cyclopentene

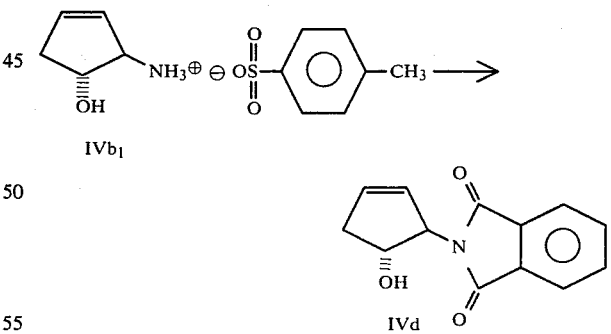

A 31.3 g. (0.115 M) quantity of dl-trans-3-amino-4-hydroxycyclopentene toluenesulfonate is dissolved in 240 ml. of tetrahydrofuran and 47 ml. (0.46 M) of triethylamine. The resultant stirred solution is cooled to 5° and treated dropwise with 22.8 g. (0.115 M) of o-methoxycarbonylbenzoylchloride. The reaction is then allowed to warm to 25°. After 48 hours the reaction is partitioned between Ethyl acetate and water. The ethyl acetate layer is dried over magnesium sulfate and concentrated in vacuo leaving 29.6 g. of residue. This residue is chromatographed over silica gel 60 eluted with 5 l. of (10–90) and 7.5 l. of (20–80) acetone-methylene chloride. Three hundred ml. fractions are collected. The product is isolated in fractions 25–35, which upon standing crystallizes to yield 14.2 g. of dl-trans-4-hydroxy-3-phthalido-cyclopentene, m.p. 114°–116°.

Preparation 6b
dl-Trans-4-hydroxy-3-phthalimidocyclopentene

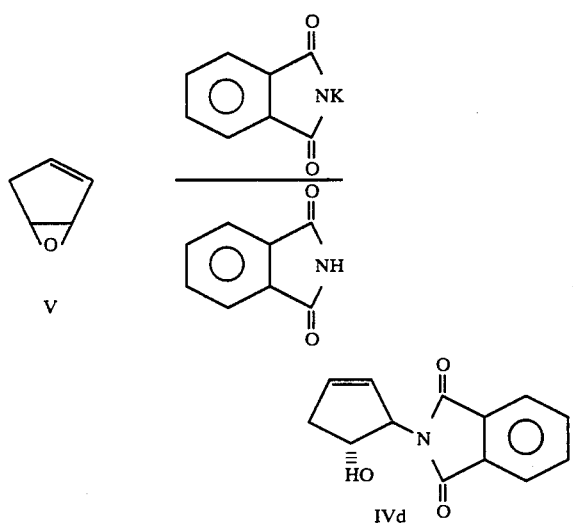

A quantity of crude dl-3,4-epoxycyclopentene is added to a suspension of 7.2 g. (49 mM) of phthalimide and 1.43 g. (7.7 mM) of potassium phthalimide in 23 ml of dry dimethylformamide. After stirring at 25° for 114 hours the reaction is treated with 0.5 ml. (8.3 mM) of acetic acid and stirred for an additional hour. The reaction is then evaporated in vacuo and the residue chromatographed over 300 g. of silica gel 60 eluted with (10–90) acetone-$CH_2Cl_2$. Fifty ml. fractions are collected. The product is collected in fractions 26–30, which upon standing crystallizes to yield 0.58 g. of dl-trans-hydroxy-3-phthalido-cyclopentene.

NMR ($CDCl_3$ δ): 2.1–3.4 (m, $CH_2$), 3.7 (OH), 4.6–5.0 (m, CHOH), 5.0–5.3 (m, CHN), 5.5–6.2 (m, CH=CH), 7.7 (s, ArH).

TLC (silica gel 60): Rf=0.32 in (40–60) ethyl acetate-Skellysolve B and Rf=0.71 in (15–85) acetone-$CH_2Cl_2$.

Anal. Calc'd. for $C_{13}H_{11}NO_3$: C, 68.14; H, 4.80. C, 68.19; H, 4.86.

Using the procedure of Preparation 6 but substituting the appropriately substituted O-methoxy carbonylbenzoylchloride or 3-methoxy carbonyl proponyl chloride for O-methoxy carbonylbenzoylchloride there is obtained
  dl-trans-4-hydroxy-3-(3-nitrophthalimido)-cyclopentene
  dl-trans-4-hydroxy-3-(4-methyl-phthalimido)-cyclopentene
  dl-trans-4-hydroxy-3-succinimide-cyclopentene
  dl-trans-4-hydroxy-3-(2,3-dimethylsuccinimidocyclopentene
  dl-trans-4-hydroxy-3-hexahydrophthalimidocyclopentene Preparation 6c

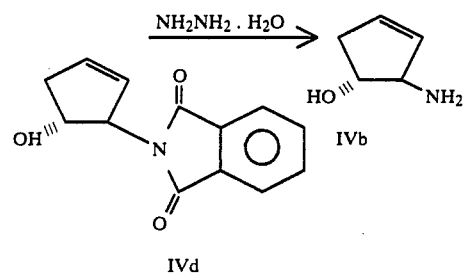

A 4.07 g. (17.67 mM) quantity of dl-trans-4-hydroxy-3-phthalido-cyclopentene is dissolved in 65 ml of tetrahydrofuran and 65 ml of ethyl alcohol. The solution is treated with 0.94 ml (0.97 g., 19.44 mM) of hydrazine hydrate. After 10 minutes a precipitate forms. After 2 hours the reaction is evaporated in vacuo (<25 mm and −30°). The residue is triturated with methylene chloride and filtered to remove the insoluble phthalhydrazide. The filtrate is concentrated in vacuo leaving dl-trans-3-amino-4-hydroxy-cyclopentene as a solid.

Preparation 7
dl-Trans-3-amino-4-hydroxycyclopentene-N-trichloroethyl urethane

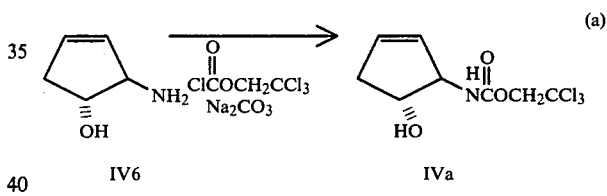

A 9.9 g. quantity of crude dl-trans-3-amino-4-hydroxycyclopentene (prepared as in Preparation 3a) is dissolved in 75 ml. of water and the mixture treated with 10.6 g. (100 mM) of sodium carbonate. The mixture is then cooled in an ice bath to <10° and treated dropwise while stirring vigorously, with 10.6 g. (50 mM) of trichloroethylchloroformate over 30 min. After 3 hours the reaction is acidified with cold concentrated hydrochloric acid. The aqueous mixture is extracted three times with methylene chloride. The methylene chloride solution is washed with water, dried over sodium sulfate and concentrated in vacuo leaving 13.2 g. of brown oil. The oil is chromatographed over 750 g. of silica dioxide eluted with (10–90) acetone-methylene chloride. Fifty ml. fractions are collected. The product is found by TLC in fractions 55–85. Concentration of these fractions yields 5.0 g. of trans-3-amino-4-hydroxycyclopentene-N-trichloroethyl urethane as crystalline solid. m.p. 100°–103°.

NMR ($CDCl_3$, δ): 1.9–3.1 (m, $CH_2$), 4.0–4.65 (m, 3H), 4.74 (s, $OCH_2$), 5.45–6.1 (m, CH=CH), 6.5–7.0 (NH).

TLC (silica gel 60): Rf=0.5 in (10–90) acetone-methylenechloride.

Preparation 7a
dl-Trans-3-amino-4-hydroxycyclopentene-N-trichloroethyl urethane

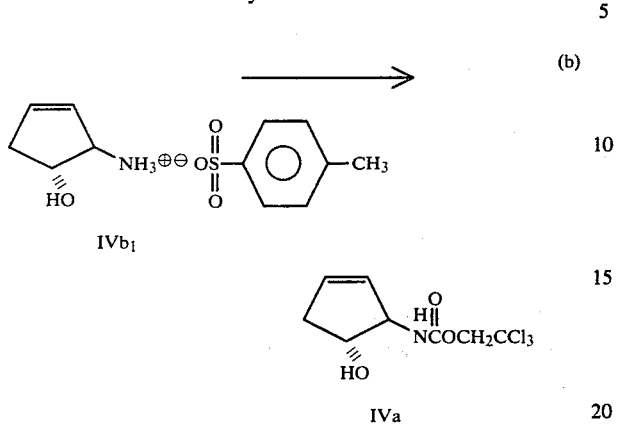

A 13.55 g. (50 mM) trans-3-amino-4-hydroxycyclopentene toluenesulfonate is dissolved in 75 ml. of water. The solution treated with 10.6 g. (10.0 mM) of sodium carbonate, cooled in an ice bath, and treated dropwise with 10.6 g. (50 mM) of trichloroethylchloroformate while stirring vigorously. After 75 min. the reaction is partitioned between water and methylene chloride. The aqueous layer is separated and extracted two times more with methylene chloride. The combined methylene chloride layer is dried over sodium sulfate and concentrated in vacuo. Crystals of trans-3-amino-4-hydroxy-cyclopentene-N-trichloroethyl urethane are formed during the concentration. These are collected three times, each time rinsing the crystals with ether crop 1, 6.12 g. m.p. 105.5°–106°; crop 2, 4.36 g., m.p. 105–106; crop 3, 1.28 g., m.p. 104–105°.

Using the same procedure as in Preparation 7 but substituting the appropriate halo-substituted alkylhaloformate or activated alkyl carbonate for trichloro ethyl formate there is obtained.

- dl-trans-3-amino-4-hydroxy cyclopentene-N-t-butyl urethane
- dl-trans-3-amino-4-hydroxy cyclopentene-N-p-methoxybenzyl urethane
- dl-trans-3-amino-4-hydroxy cyclopentene-N-diphenylmethyl urethane
- dl-trans-3-amino-4-hydroxycyclopentene-N-[2-iodoethyl urethane Using the same procedure as in Preparation 7 but substituting benzyloxychloroformate there is obtained dl-trans-3-(O-benzylcarbamoyl)-4-hydroxycyclopentene after chromatography on silic gel with 85% methylene chloride/acetone.

NMR (CDCl$_3$)=2.1–2.9 (m, CH$_2$), 3.8–4.6 (m, 3H), 5.02 (5, OCH$_2$), 5.3–6.0 (m, 3H), 7.22 (s, Ph).

TLC: Rf=0.58 (15% acetone/methylene chloride). Similarly prepared is the optically active (d) trans-5-(O-benzylcarbamoyl)-4-hydroxy cyclopentene by substituting the d-starting material for the racemic.

Preparation 8 dl-2,2,2-Trichloroethyl cis-5-(phthalimidoxy)-2-cyclopentene-1-carbamate

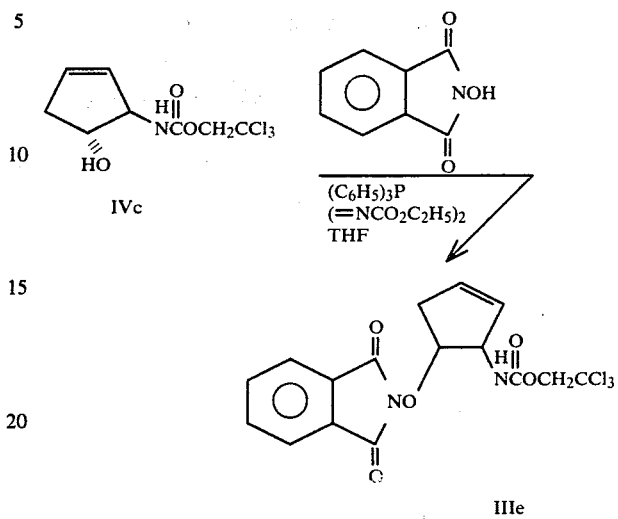

An 11.75 g. (42.8 mM) quantity of dl-trans-3-amino-4-hydroxy-cyclopentene-N-trichloroethyl urethane, a 7.86 g. (48.3 mM) quantity of N-hydroxyphthalimide, and a 12.63 g. (48.3 mM) quantity of triphenylphosphine are dissolved in 210 ml. of tetrahydrofurane dry. To the stirred solution is added dropwise over 15 minutes 9.21 g. (53.1 mM) of diethylazodicarboxylates while holding the temperature below 35° with an ice bath. The reaction is then stirred for 1 hour at 25°, after which it is concentrated in vacuo (~ <25 mm. and ~30°). The residue is treated with ~100 ml. of (10–60) ethyl acetate-Skellysolve B and the precipitated triphenylphosphine oxide removed by filtration after about 15 minutes. The residue is added to the top of a 1 kg. silica gel 60 column which is eluted with 3 l. of (40–60) followed by (50—50) ethyl acetate-Skellysolve B. Three hundred ml. fractions are collected. Fractions 14–19 are found to contain pure dl-2,2,2-trichloroethyl cis-5-(phthalimidoxy) 2-cyclopentene-1-carbamate by TLC. On concentration they yield 6.24 g. of crystals as a first crop, m.p. 138.5–139.5, 2.8 g. of a second crop m.p. 138.5°–139.5° and left 2.13 g. of residue on evaporation to dryness. Fractions 20–24 are found to contain by TLC a more polar impurity. These fractions are combined with the 2.13 g. of residue from above and rechromatographed over 750 g. of silica gel 6q which is eluted with (10–90) ethyl acetate benzene. Three hundred ml. fractions are collected Fractions 8–13 are found by TLC to contain product. Concentration of these fractions produced two more crops of dl-2,2,2-trichloroethyl cis-5-(phthalimidoxy)-2-cyclopentene-1-carbamate crystals of 2.75 g. and 2.62 g. with m.p.s of 138.5°–139.5° and 137.5°–138.5°, respectively. Total yield 14.41 g.

NMR (CDCl$_3$, δ): 2.65–3.0 (m, CH$_2$), 4.77 (s, OCH$_2$) 4.7–5.2 (m, 2H), 5.7–6.1 (m, CH═CH), 6.35–6.75 (NH), 7.83 (s, ArH).

TLC (silica gel 60): Rf=0.55 in (40–60) ethyl acetate Skellysolve B and Rf=0.47 in (10–90) ethyl acetate-benzene.

Anal. Calc'd for C$_{18}$H$_{18}$Cl$_3$N$_2$O$_5$: C, 45.79; H, 3.12; N, 6.68; Cl, 25.35 Found: C, 45.92; H, 3.13; N, 6.62; Cl, 25.47.

Using the same procedure as in Preparation 8 but substituting the appropriate dl-trans-3-amino-4-hydroxycyclopentene-N-haloalkyl urethane for dl-trans-3-amino-4-hydroxycyclopentene-N-trichloroethyl urethane there is obtained dl-t-butyl-cis-5-(phthalimidoxy)-2-cyclopentene-1-carbamate,
  dl-p-methoxybenzyl-cis-5-(phthalimidoxy-2-cyclopentene-1-carbamate,
  dl-diphenylmethyl-cis-5-(phthalimidoxy)-2-cyclopenetene-1-carbamate, Using the same procedure as in Preparation 8 but substituting the appropriate N-hydroxyphthalimides and N-hydroxysuccimides for N-hydroxyphthalimide there is obtained dl-(2,2,2-trichloroethyl)-cis-5-(3-nitrophthalimidooxy)-2-cyclopentene-1-carbamate,
  dl-(2,2,2-trichloroethyl)-cis-5-(3-nitrophthalimido)-2-cyclopentene-1-carbamate,
  dl-(2,2,2-trichloroethyl)-cis-5-(succinimidoxy)-2-cyclopentene-1-carbamate,
  dl-(2,2,2-trichloroethyl)-cis-5-(2,3-dimethyl-succinimidoxy)-2-cyclopentene-1-carbamate, Using the same procedure as outlined in Preparation 8 but using various alkyl methanes and substituted n-hydroxyphthalimides and n-hydroxysuccinimides there is obtained dl-benzyl(cis-5-(3-nitrophthalimidoxy)-2-cyclopentene-1-carbamate
  dl-p-methoxybenzyl-cis-5-(4-methylphthalimidoxy)-cyclopentene-1-carbamate.

Preparation 9 dl-Benzyl cis-5-(phthalimidoxy)-2-cyclopentene-1-carbamate

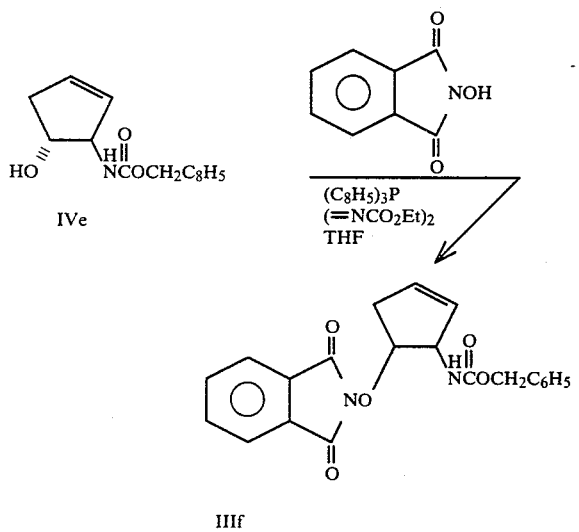

A 1.46 g. (6.26 mM) quantity of trans-3-amino-cyclopentene-N-benzyl urethane, a 1.12 g. (6.88 mM) quantity of N-hydroxyphthalimide, and 1.8 g. (6.88 mM) of triphenylphosphine are dissolved in 25 ml. of dry tetrahydrofuran. The solution is treated dropwise over about 5 min. with 1.32 g. (7.6 mM) of diethyl azodicarboxylate in 5 ml. of tetrahydrofuran. The initial red solution after the start of the addition turns yellow in about 10 minutes. After 16 hours the reaction is concentrated in vacuo (<25 mm at ~30°) and the residue chromatographed over 150 g. of silica gel. The column is eluted with 40 ml. of (20–80) followed by (25–75) ethyl acetate benzene. Twenty-five ml. fractions are collected. The product is found by TLC ion fractions 13–20. Concentration of these fractions left 1.76 g. of dl-benzyl cis-5-(phthalimidoxy)-2-cyclopentene-1-carbamate as an oil which crystallizes on standing. Recrystallization n from 50% ethyl acetate/hexane gives m.p. 120°-2°.

NMR (CDCl$_3$, δ): 2.65–2.95 (m, CH$_2$), 4.8–5.10 (m, 2H), 5.15 (s, OCH$_2$), 5.65–6.1 (m, CH=CH), 6.1–6.4 (NH), 7.37 (s, 5, ArH), 7.78 (s, 4, ArH).

TLC (silica gel 60): Rf=0.65 in (25–75) ethyl acetate benzene and Rf=0.72 in (5–95) acetone-methylene chloride.

Elemental Analysis for C$_{21}$H$_{18}$N$_2$O$_5$ Calc'd: C, 66.65; H, 4.79; N, 7.41. Found: C, 66.16; H, 4.84; N, 7.32.

Using the same procedure, the d-benzyl-cis-5-(phthalimidoxy)-2-cyclopentene-1-carbamate is prepared by substituting the d-starting material for the racemic mixture.

Preparation 10 dl-2,2,2-Trichloroethyl cis-5-(aminooxy)-2-cyclopentene-1-carbamate

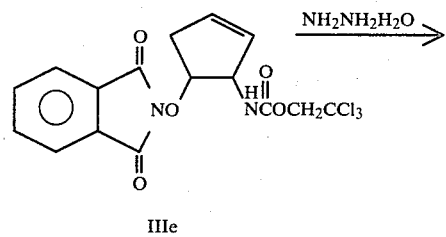

IIIe

IIId

A 7.42 g. (17.67 mM) quantity of dl-2,2,2-trichloroethyl trans-5-(phthalimidoxy)-2-cyclopentene-1-carbamate is dissolved in 65 ml. of tetrahydrofuran and 65 ml. of ethyl alcohol. The solution is treated with 0.94 ml. (0.97 g., 19.44 mM) of hydrazine hydrate. After 10 minutes a precipitate forms. After 2 hours the reaction is evaporated in vacuo (<25 mn and ~30°). The residue is triturated with methylene chloride and filtered to remove the insoluble phthalhydrazide. The filtrate is concentrated in vacuo leaving 6.68 g. of dl-2,2,2-trichloroethyl cis-5-(aminooxy)-2-cyclopentene-1-carbamate as an oil.

NMR (CDCl$_3$, δ): 2.35–2.65 (m, CH$_2$), 4.1–4.95 (m, 2H), 4.78 (s, OCH$_2$), 5.35–6.1 (m, 5, NH, NH$_2$, (CH=CH).

TLC (silica gel 60): Rf=0.41 in (5–95) methanol-benzene and Rf=0.41 in (40–60) ethyl acetate Skellysolve B.

Using the same procedure as in Preparation 10, but substituting other dl haloalkyl trans-5-(phthalimidoxy)-2-cyclopentene-1-carbamates for dl-2,2,2-trichloroethyl trans-5-(phthalimidoxy)-2-cyclopentene-1-carbamates there are obtained corresponding halo alkyl cis-5-(amino-oxy)-2-cyclopentene-1-carbamates.

Using the same procedure as in Preparation 10 but substituting dl or d-benzyl-cis-5-(phthalimidoxy)-2-cyclopentene-1-carbamate there is obtained dl or d (resp.) benzyl-cis-5-(aminooxy)-2-cyclopentene-1-carbamate. The Rf=0.40 (50% ethyl acetate/hexane) (starting material Rf=0.71.

Preparation 11 dl-2,2,2-Trichloroethyl cis-[[[(benzyloxy)carbonyl]amino]oxy]-2-cyclopentene-1-carbamate

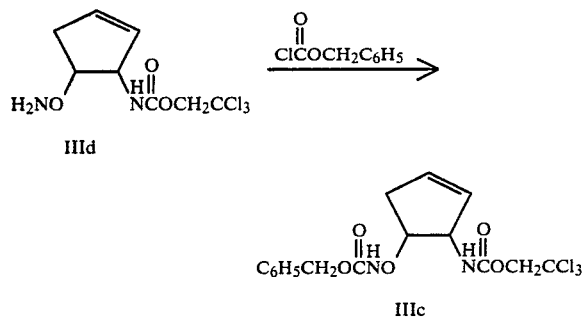

The crude dl-2,2,2-trichloroethyl cis-5-aminooxy-2-cyclopentene-1-carbamate (1.6 SmM) prepared in preparation 10 is dissolved in 10 ml. of pyridine and the solution cooled in an ice bath and treated with 0.34 g (2.0 mM) of benzyloxychloroformate dissolved in 2 ml of CH$_2$Cl$_2$. After 1.5 hours the reaction mixture is poured into water and methylene chloride and treated with (ammonium chloride until acidic). The methylene chloride layer is separated, dried over sodium sulfate and concentrated in vacuo leaving 766 mg of oil. The oil is chromatographed over 55 g of silica gel 60, eluted with (40-60) ethyl acetate-Skellysolve B. Then ml fractions are collected. Fractions 10-13, which are shown by TLC to contain the product, are combined and concentrated in vacuo leaving 535 mg of residue. After addition of isopropylether to the residue and scratching, the material crystallized to yield dl-2,2,2-trichloroethyl cis-[[[(benzyloxy)carbonyl]amino]oxy]-2-cyclopentene-1-carbamate, m.p. 86°-89° C.

NMR (CDCl$_3$, δ): 2.2-2.9 (m, 2H), 4.2-5.0 (m, CHN, CHO), 4.67 (s, OCH$_2$CCl$_3$), 5.16 (s, OCH$_2$φ), 5.4-6.2 (m, CH=CH), 7.37 (s, φ), 7.6-8.0 (m, NH), 8.47 (s, NH).

TLC (silica gel 60): Rf=0.73 in (40-60) ethylacetate-Skellysolve B.

Using the same procedure as in Preparation 11 but substituting either dl or (1R,5S)-benzyl-cis-5-(aminooxy)-2-cyclopentene-1-carbonate for IIId and 2,2,2-trichloroethylchloroformate for benzyloxychloroformate there is obtained dl or d (resp.) benzyl-cis[[(2,2,2-trichloroethoxy)carbonyl)aminooxy]-2-cyclopentene-1-carbamate.

NMR (CDCl3): 7.30 (s, pH), 5.6-61 (m, 2H), 5.10 (5, OCH$_2$), 44-5.0 (m, 2H), 4.72 (s, CCl$_3$CH$_2$), 2.4-2.8 (m, 2H).

TLC: Rf=0.83 (50% ethylacetate/hexane)

Preparation 12 dl-Benzyl cis-[(2-amino-3-cyclopenten-1-yl)oxy]carbamate

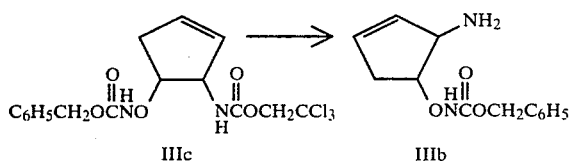

(a) Zinc, Ammonium Chloride, Methanol Procedure

A 21.32 g (50.4 mM) quantity of dl-2,2,2-trichloroethyl cis-[[[(benzyloxy)carbonyl]amino]oxy]-2-cyclopentene-1-carbonate is dissolved in 425 ml of methanol and the solution treated with 21.3 g (326 mM) of zinc and 10.7 g (200 mM) of ammonium chloride. The resultant mixture is stirred vigorously for 60 minutes at which time TLC showed the reaction to be complete. The reaction is mildly exothermic and on the scale described warmed from a temperature of 25° at the start of the reaction to a maximum of 35° C. The reaction mixture is then filtered and the filtrate concentrated in vacuo. The filtered solids are washed with about 200 ml of 5% sodium bisulfate (aqueous) and this washing is added to the residue from evaporation of the methanol. The resultant aqueous mixture is partitioned between methylene chloride and the methylene chloride layer is separated. The aqueous layer is made basic to pH8 with conc. ammonium hydroxide and then is treated with 4 g of sodium cyanide and the resultant solution extracted 3 times with ~200 ml portions of methylene chloride. The combined methylene chloride solutions are dried over sodium sulfate and concentrated in vacuo to yield 9.6 g (77%) of benzyl cis-[(2-amino-3-cyclopenten-1-yl)oxy]carbamate as an oil.

NMR (CDCl$_3$, δ): 2.2-2.7 (m, 2H), 3.6-5.5 (m), 5.08 (s, OCH$_2$), 5.5-5.9 (m, CH=CH), 7.28 (s, 5Ar-H).

TLC (silica gel 60): Rf=0.42 in (1-10-90) ammonium hydroxide-methanol-methylene chloride.

The reaction produces zinc complexes of product dl-benzyl cis-[(2-amino-3-cyclopenten-1-yl)oxy]carbamate which are insoluble in MeOH and most other organic solvents. These can be dissolved in aqueous acid.

The compound under basic pH makes strong complexes with zinc. The product can be extracted from aqueous only if the complexes are broken up. EDTA tetra sodium salt also works but not as well as sodium cyanide.

(b) Zinc, Ammonium Chloride, Methanol, Sodium Hydroxide Workup.

The zinc, ammonium chloride reduction in methanol is run as above in procedure (a) on a 17.67 mM quantity of dl-2,2,2-trichloroethyl cis-[[[(benzyloxy)carbonyl]amino]-oxy]-2-cyclopentene-1-carbamate. After the extraction of the acidic aqueous solution to remove dichloro by-product, the aqueous is made basic to pH 14 with 50% sodium hydroxide (using ice to keep the mixture cool). At pH~8-10 a volumous precipitate of zinc hydroxide forms but this redissolves at higher pH leaving the zinc salt of the desired product. This salt is insoluble in most solvents except for aqueous acid. The resultant precipitate is filtered and dried. This zinc salt of dl-benzyl cis[(2-amino-3-cyclopenten-1-yl)oxy]carbamate is dissolved in the minimum amount of ammonium chloride to effect solution. This is then freeze-dried and the residue used in Preparation 13a.

(c) Zinc, Methane Sulfonic Acid, Methanol Procedure

A 10 g. (23.6 mM) quantity of dl-2,2,2-trichloroethyl cis[[[(benzyloxy)carbonyl]amino]oxy-2-cyclopentene-1-carbamate is dissolved in 200 ml. of methanol. The solution is treated with 10 g. (154 mM) of zinc dust. To this mixture is added over 25 minutes, while stirring vigorously. 4 ml. of methanesulfonic acid. TLC shows the reaction to be complete in less than 1 hour. The reaction mixture is then filtered and the zinc solids washed with methanol. The filtrate and combined washings are concentrated in vacuo and the residue is used directly in Preparation 13.

(d) Zinc, Acetic Acid, Water Procedure.

A 1.0 g. (2.36 mM) quantity of dl-2,2,2-trichloroethyl cis[[[(benzyloxy)carbonyl]amino]oxy]cyclopentene-1-carbamate is dissolved in 10 ml of (9-1) acetic-acid water and the solution treated with a total of 1.0 g (15.4 mM) of zinc added in 5 equal portions in 45 min intervals. After a total of 6 hours from the initial addition, TLC shows the reaction to be complete. The reaction mixture is then filtered and the filtrate partitioned between 5% sodium bisulfate and methylene chloride. The aqueous layer is separated and made basic to pH 9–10 with conc. ammonium hydroxide using ice to keep the mixture cool. The resultant aqueous solution is extracted three times with methylene chloride. The combined methylene chloride solutions are dried over sodium sulfate and concentrated in vacuo leaving 516 mg (88%) of dl-benzyl cis-[(2-amino-3-cyclopenten-1-yl)oxy]carbamate as an oil.

In the acetic acid runs, NH4OH seems to be adequate to break up the zinc salts. NH4OH is not sufficient for the products from procedures 12(a) and 12(c).

Preparation 13
dl-Benzyl-cis-(2-phthalimido-3-(cyclopenten-1-yl)oxy]-carbamate (30)

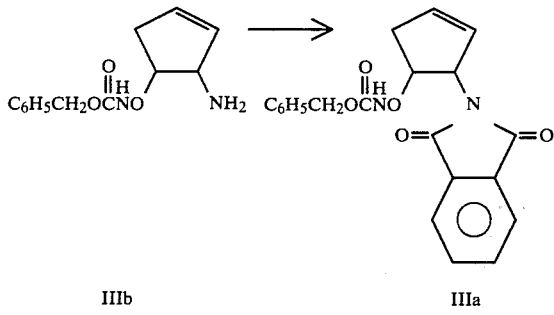

IIIb      IIIa (a) An 11.6 g (46.6mM) quantity of crude benzyl-cis-([2-amino-3-cyclopenten-1-yl)oxy]carbamate from step 34 procedure (a) is dissolved in 250 ml of tetrahydrofuran. To this is added 11.5 g (58.3 mM) of 2-methoxy carbonylbenzoyl chloride solved in 250 ml of tetrahydrofuran. To this is added 11.5 g (58.3 mM) of 2-methoxy carbonylbenzoyl chloride and 31 ml (23.5 g, 232 mM) of triethylamine. The reaction is warmed to 50° for 72 hours at which time TLC indicates the reaction has gone to completion. The reaction is then concentrated in vacuo. The residue is partitioned between ethyl acetate and ammonium chloride. The ethyl acetate layer is separated and washed with 5% sodium bisulfate and water and dried over magnesium sulfate. Concentration of the ethyl acetate solution in vacuo leaves 22.9 g of crude residue. The residue is chromatographed over 2 kg of silica gel 60 eluted with (40–60) ethyl acetate-Skellysolve B. Four hundred ml fractions are collected after taking a forerun of 2 l. The product is found in fr 16–24 by TLC. Concentration of these fractions gives 13.15 g (75%) of dl cis-[2-phthalamido-3-(cyclopenten-yl)oxy]carbamate.

NMR (CDCl3, δ): 2.4–3.2 (m, CH2), 4.5–5.5 (m, 4), 5.00 (s, oCH2), 5.5–6.2 (m, CH=CH), 7.27 (s, 5ArH), 7.5–8.0 (m, 4ArH).

TLC (silica gel 60) Rf=0.48 in (40-60) ethyl acetate-Skellysolve B.

(b) Using the same procedure as in (a) above on 17.67 the crude dl-benzyl-cis-[(2-amino-3-cyclopenten-1-yl)oxy]carbamate Zn salts, a 3.23 g. (48%) yield of cis-[2-phthalimido-3-cyclopenten-1-yl)oxy]carbamate is obtained.

(c) Using the same procedure as in (a) and (b) above on 23.6 mM of dl-benzyl-cis[(2-amino-3-cyclopenten-1-yl)-oxy]carbamate, a 6.91 g. (77%) yield of dl-cis[(2-phthalimido-3-cyclopenten-1-yl)oxy]carbamate is obtained.

The combined steps 12(c) and 13(c) are the preferred method for converting dl-2,2,2-trichloroethyl cis-[[[(benzyloxy)carbonyl]amino]oxy]-2-cyclopentene-1-carbamate to dl-benzyl-cis-[2-phthalimido-3-(cyclopenten-1-yl)oxy]carbamate.

In addition, both dl- and d-cis-(2-phthalimido-3-[cyclopenten-1-(2,2,2-trichloroethoxycarbonyl)aminooxy]-carbamate can be prepared by using Preparation 13 but substituting dl- or d-2,2,2-trichloroethyl-cis-[(2-amino-3-cyclopenten-1-yl]oxy]carbamate. This substituted starting material can be prepared by treating dl or d (resp)benzyl-cis[([2,2,2-trichloroethoxy]carbonyl-)aminooxy]-2-cyclopentene-1-carbamate (prepared by Preparation 11) with HBr saturated glacial acetic acid for one hour at room temperature. The reaction solution is concentrated in vacuo to afford the product which can be used directly as above in Preparation 13.

NMR (CDCl3): 7.5–8.0 (m, 4H), 8.45 (m, NH), 5.5–6.2 (m, 2H), 4.3–5.5 (m, 4H), 4.69 (s, CCl3CH2), 2.6–3.0 (m, 2H).

TLC: Rf=6.67 (50% ethylacetate/hexane)

Preparation 14 (αS,5S and αR,5R)-2-[(benzyloxy)carbonyl]-3-oxo-α-phthalimido-5-isoxazolidine-acetic acid

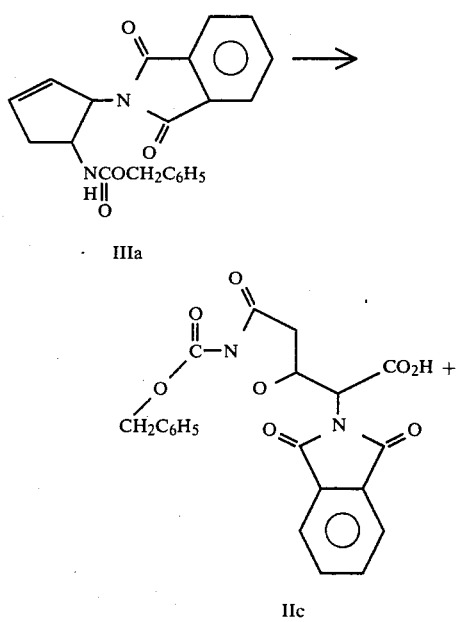

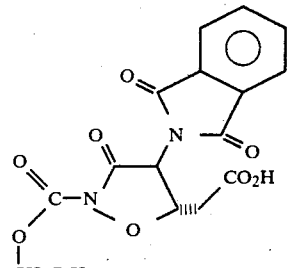

VIId

An 10.0 g (26.5 mM) quantity of dl-cis-[2-phthalimido-3-cyclopenten-1-yl)oxy]carbamate IIIa is dissolved in 250 ml of acetone and 180 ml of water. The resultant solution is treated with 28 g (130 mM) of sodium iodate and 100 mg of ruthenium chloride hydrate (1-3 $H_2O$) in 5 ml. of water. The reaction is stirred vigorously for one hour. After about the first 15 minutes a slight exotherm occurs causing the temperature to rise from about room temperature (~23°) to about 35°. The reaction is then evaporated at <30 mm and <30° C. to remove acetone. The aqueous residue is partitioned between ethyl acetate and water acidified with ~10 ml of M sulfuric acid. The aqueous layer is separated and extracted 2 times more with ethylacetate. The combined ethylacetate solutions are washed with saturated sodium chloride solution, dried over magnesium sulfate and concentrated in vacuo (<30 mm, <30° C.) leaving a glassy foam. The residue is chromatographed over 1 kg of CC-4 silica gel eluted with a linear gradient prepared from 5 l of (40-60) ethyl acetate-Skellysolve B and 5 l of (80-20) ethyl acetate-Skellysolve B. Fractions (400 ml) 16-19 yield 7.48 g. of essentially pure (α5,5S and 2R,5R)-2-[(benzyloxy)-carbonyl]-3-oxo-α-phthalimido-5-isoxazoline acetic acid, m.p. 113°-116° (from ethanol).

NMR $d_6$-acetone, δ): 3.16 (d, J=7.5, $CH_2$), 5.25 (s, $OCH_2$), 5.1-5.7 (m, 2), 7.39 (s, 5), 7.92 (s, 4).

Elemental Analysis: Calc'd for $C_{21}H_{16}N_2O_8$ Calc'd: C, 59.43; H, 3.80; N, 6.60. Found: C, 58.79; H, 3.80; N, 6.53.

Fraction 14 yields 0.93 g of 2-[(Benzyloxy)-carbonyl]-3-oxo-4-phthalimido-5-isoxazolidine acetic acid, m.p. 160°-2° (ethyl acetate/hexane, 1:1).

NMR $d_6$-acetone, δ): 3.06 (d, J=5.5, $CH_2$), 5.38 (s, $OCH_2$), 5.1-5.8 (m, 2), 7.45 (m, 5) 7.88 (s, 4).

Elemental Analysis: Calc'd for $C_{21}H_{16}N_2O_8 \cdot H_2O$ Calc'd: C, 57.01; H, 4.10; N, 6.33. Found: C, 57.24; H, 3.98; N, 6.45.

A mixture of the two acids is found in Fraction 15.

Using the same procedure as in Preparation 14 but substituting dl- or d-cis-(2-phthalimido)-3-[cyclopentene-1-(2,2,2-trichloroethoxycarbony)aminooxy]carbamate affords (α5,5S and αR,5R)-2-[(2,2,2-trichloroethoxy)carbonyl]-3-oxo-α-phthalimido-5-isoxazolidine-acetic acid (57% yield), m.p. 208°-210°.

NMR (acetone-$d_6$): 3.27 (d, J=7.5 Hz, $CH_2$), 4.92 (s, $CCl_3CH_2$), 5.1-5.7 (m, 2H), 7.91 (s, 4H).

TLC: Rf=0.41 (A IX)

Analysis: Calc'd for $C_{16}H_{11}Cl_3N_2O_8$ Calc'd: C, 41.27; H, 2.38; N, 6.02. Found: C, 41.33; H, 2.36; N, 6.04.

The isomeric (4S,5S and 4R,5R)-2-[(2,2,2-trichloroethoxy)carbonyl]-3-oxo-4-phthalimido-5-isoxazolidine acetic acid is also produced in 22% yield.

NMR (acetone-$d_6$): 3.10 (d, J=5.5 $H_3$, 2H), 5.08 (5, $CCl_3CH_2$), 5.1-5.8 (m, 2H), 7.90 (s, 4H).

TLC: Rf=6.52

Preparation 15 (α5,5S and αR,5R)-3-Oxo-α-phthalimido-5-isoxazolidine acetic acid

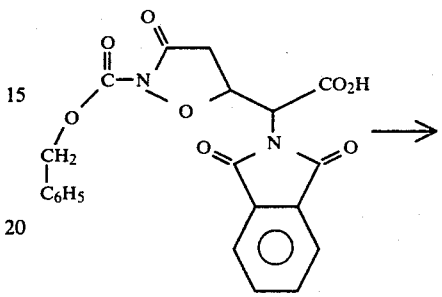

IIc

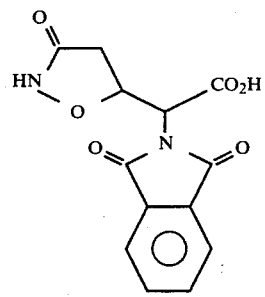

IIb

A 7.48 g 17.6 mM) quantity of (αS,5S and αR,5R)-2-[(benzyloxy)carbonyl]-3-oxo-α-phthalimido-5-isoxazolidine acetic acid is dissolved in 150 ml. of ethyl acetate and 75 ml. of 95% ethanol. The solution is treated with 1.5 g. of palladium black and hydrogenated at 25° C. and 1 atmosphere of pressure. The reaction is stopped after 165 minutes, filtered and the filtrate used directly for the preparation of (αS,5S and αR,5R)-3-oxo-α-phthalimido-5-isoxazolidine acetic acid.

Using the same procedure as above in a different run the filtrate is evaporated in vacuo to yield (αS,5S and αR,5R)-3-oxo-α-phthalimido-5-isoxazolidine acetic acid as a residue.

NMR ($CD_3OD$, δ): 2.92 (partially split d, $CH_2$), 5.1-5.7 (m, 2), 7.85 (s, 4 ArH).

TLC (silica gel 60): Rf=0.36 in the upper phase of (9-2-5-10) ethylacetate-acetic acid cyclohexane-water. In the same system the starting material Rf=0.46

Using the same procedure as in Preparation 15 with dl or d VIIId affords the dl or d (resp.) isotricholomic acid phthalimide VIIc as a white foam with TLC $R_f$=0.54 (starting material $R_f$=0.64)

NMR (Acetone-$d_6$): 9.1 (s, $CO_2H$), 7.83 (s, 4H), 5.0-5.8 (m, 2H), 2.95 (m, 2H).

Alternatively, the benzyloxycarbonyl group can be removed from IIc to produce IIb (or VIId to VIIc) with acid. For example, a 424 mg (1 mmole) amount of IIb is dissolved in 5 ml of glacial acetic acid under $N_2$ and dry HBr is bubbled into the reaction solution for 10 minutes. After stirring for 4 hours at room temperature the solution is concentrated over chromatographed on 50 g of CC-4 silica gel with 70% ethylacetate/hexane. This procedure yielded 170 mg (59%) of product identical to that produced hydrogenolytically (by NMR and TLC). Other acids and solvents such as HBr/CH$_3$NO$_2$, HBR/CH$_2$Cl$_2$ and trifluoroacetic acid can also be employed.

Preparation 16 ($\alpha$S,5S and $\alpha$R,5R)-3-oxo-$\alpha$-phthalimido-5-isoxazolidine acetic acid, benzhydryl ester

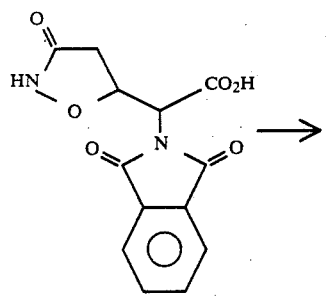

IIb

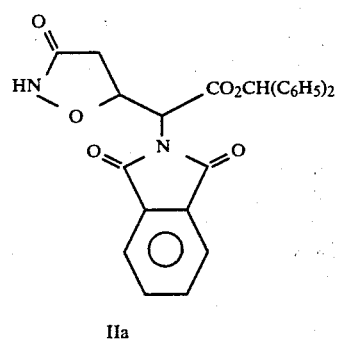

IIa

A 5.2 g (26.5 mM) quantity of benzophenone hydrazone was dissolved in 125 ml of ethyl ether. The solution is treated with 10 g of sodium sulfate, 11.1 g (51 mM) of yellow mecury oxide and 0.2 ml of a saturated potassium hydroxide solution in ethyl alcohol. The reaction is stirred 60 minutes and the resultant deep burgandy mixture filtered. The resultant solution is added directly to the reaction solution from a 17.6 mM hydrogenation in which ($\alpha$S,5S and $\alpha$R,5R)-3-oxo-$\alpha$-phthalimide-5-isoxazolidine acetic acid is prepared. TLC shows the reaction to be finished in less than one hour. The reaction is then treated with sufficient 3 N hydrochloric acid while stirring vigorously, to destroy the excess burgundy colored diazo compounds. The reaction mixture is then evaporated in vacuo (<30 mm and <30° C.). and chromatographed over 500 g. of CC-4 silica gel eluted with (40–60) ethyl acetate-toluene. Two hundred ml. fractions are collected. The ($\alpha$S,5S and $\alpha$R,5R)-3-oxo-phthalimido-5-isoxazolidine-acetic acid, benzhydryl ester is found in fr 10–14 (3.05 g., 38% yield).

NMR (CDCl$_3$ $\delta$): 2.75 (d, J=11.5, CH$_2$), 5.15–5.7 (m, 2), 6.93 (s, CH (C$_6$H$_5$)$_2$), 7.18 (s, C$_6$H$_5$), 7.28 (s, C$_6$H$_5$), 7.5–8.0 (m, 4, ArH).

TLC (silica gel 60): Rf=0.42 in (40–60) ethyl acetate-toluene. The iso product from compound 33 has Rf=0.59 in this same system Utilizing the procedure similar to the procedure of Preparation 16, but substituting RN$_2$ for diphenyldiazomethane, where R can be methyl, ethyl, benzyl and the like, produces the corresponding esters of IIb. With these more reactive alkyl diazo compounds it is more efficient to treat the acid, IIb, in a non-protic solvent, such as tetrahydrofuran, in place of ethanol.

Alternatively, esters of IIb can be produced by alkylation of the acid in base with a reactive alkylating agent. For example, a 87 mg (0.3 mmole) quantity of IIb in 3 ml of dry acetonitrile under nitrogen is treated with 50 $\mu$l of diisopropylethylamine and 60 mg of p-methoxybenzyl bromide. After 16 hours the solution is distributed between ethyl acetate/water, and the organic phase separated dried over sodium sulfate and concentrated. Preparative TLC (50% ethyl acetate/hexane) affords 55 mg (45%) of the p-methoxybenzyl ester.

NMR (CDCl$_3$): 7.81 (m, 4H), 7.05 (A$_2$B$_2$,4H), 5.1–5.7 (, 2H), 5.13 (s, 2H), 3.76 (s, 3H, CH$_3$O), 2.81 (d, J=7.5 H$_3$, 2H).

Utilizing procedures detailed above but substituting the dl- or d-isotrichlomic acid phthalmide VIIc for IIc affords dl- d (respectively)- VIIIb, isotrichlomic phthalimide ester.

Preparation 17
dl-Trans-3-phthalimido-4-fluoromethanesulfonyloxycyclopentene

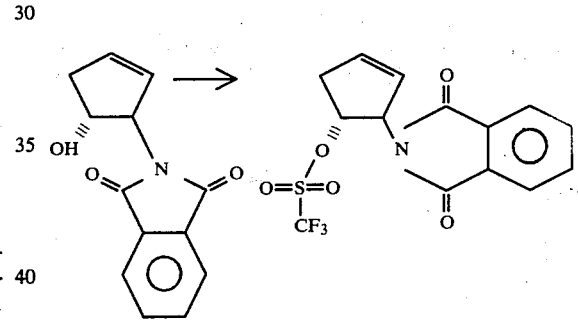

A 5 g (21.8 mM) quantity of 4-hydroxy-3-phthalimidocyclopentene and 1.72 g (21.8 mM) of pyridine are dissolved in 6 ml of methylene chloride and the solution added dropwise over 40 minutes to an ice-cooled stirred solution of 4.6 g (21.8 mM) of trifluoromethanesulfonic anhydride in 15 ml of methylene chloride under nitrogen. The solution is stirred for an additional 15 minutes and then washed with water and dried concentration of the methylene chloride solution leaves dl-trans-3-phthalimido-4-trifluoromethanesulfonyloxycyclopentene.

Preparation 18
dl-Benzyl(cis-[(2-phthalimido-3-cyclopentene-yl)oxy]-carbamate

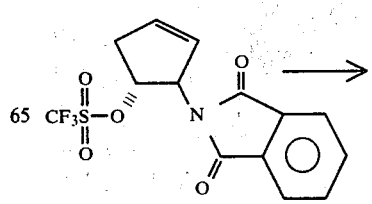

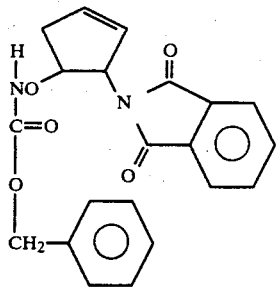

A 21.8 mM quantity of dl-trans-3-phthalimido-4-trifluoromethanesulfonyloxycyclopentene is dissolved in 50 ml of methylene chloride and the solution treated with 21.8 mM of the potassium salt of N-hydroxybenzylurethane. After stirring 24 hours under nitrogen the reaction is extracted with 5% aqeuous sodium bicarbonate and water and dried. Distillation of the methane chloride leaves a residue which is chromatographed over silica gel, eluted with (40-60) ethylacetate-Skellysolve B. After concentration of the fraction found by TLC, to contain product, there is obtained d-benyl-cis-[(2-phthalimido-3-cyclopentene-yl)oxy]carbamate.

PREPARATION OF OPTICALLY ACTIVE ISOMERS

Preparation 17 Resolution
dl-trans-3-amino-4-hydroxycyclopentene (5):
Preparation of (+)-deoxycholate 6b and (−) tartarate 6c

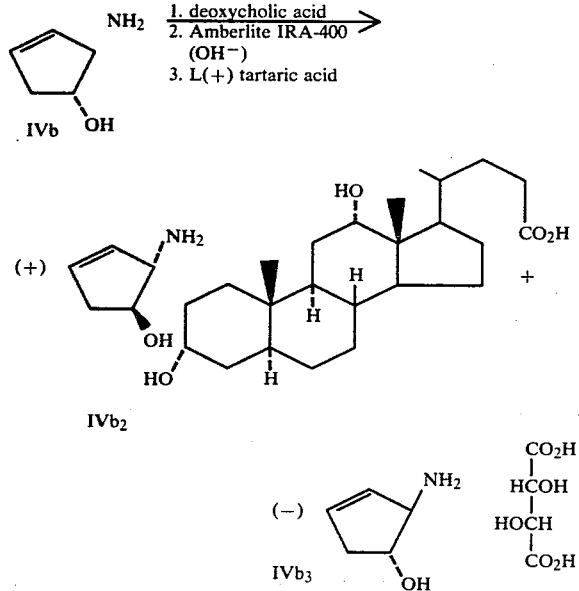

(1) A 49.5 g (0.50 M) quantity of dl trans-3-aminohydroxycyclopentene dissolved in about 100-200 ml of methanol and 98 g (0.25 M) of deoxycholic acid dissolved in about 200-300 ml of methanol are mixed and allowed to crystallize for several hours. The crystals of trans-3-amino-4-hydroxycyclopentene are collected by filtration and washed three times with some portions of methanol. There is obtained 105 g of trans-3-amino-4-hydroxycyclopentene deoxycholate as light beige crystals, m.p. 195°-197° (dec). The mother liquors are saved for Step 2.

(2) A 500 ml quantity of Amberlite IRA-400 (Cl⁻ form) is added to a 600 ml fritted funnel and washed six times with 200 ml portions of N sodium hydrochloride, 3 times with water (3×200 ml), with 200 ml portions of water three times with methanol. A 250 ml quantity of this hydroxy resin and the mother liquors from Step 1 above are mixed and stirred for 2 hours under nitrogen. The mixture is then poured on top of the other 250 ml of resin packed into a chromatography column in methanol. The column is eluted with methanol collecting 250 ml fractions. The product is found by TLC in fractions 106. Evaporation of these fractions leaves 32 g of (3R,4R)-3-amino-4-hydroxycyclopentene.

TLC (silica gel 60): Rf=0.24 in (1-20-80) ammonium hydroxide-methanol $CH_2Cl_2$. Detected by potassium permanganate spray.

(3) The residue from Step 2 above is dissolved in 300 ml. of 95% ethanol and the solution mixed with a solution of 37.5 g (0.25 M) of L-(+)-tartaric acid dissolved in 300 ml. of 95% ethanol. The mixed solutions are seeded with previously resolved salt. After 2-3 hours, the crystals are collected by filtration and dried. There is thus obtained 54.4 g of crystals, m.p. 84°-86°. The crystals are recrystallized from 700 ml of 95% ethanol. There is thus obtained 48.5 g of crystalline (3R,4R)-3-amino-4-hydroxycyclopentene L(+)-tartaric acid salt. m.p. 86.5°-88.5° $[\alpha]_{578}^{20}=-37.8°$ (c=3.20 in 4) A 200 ml quantity of Amberlite IRA-400 (OH⁻ form) and 300 mloof methanol was added to 25 g of resolved tartarate salt from step 3. The mixture is stirred under a nitrogen atmosphere for 1 hours. Another 100 ml of Amberlite IRA-400 (OH⁻ form) is added to a chromatography column and the above mixture of tartarate salt, Amberlite resin and supernatant methanol solution added to the top. The methanol is drained from the column and fresh methanol is passed through until a total of 1500 ml of methanol is collected. The methanol solution is then evaporated in vacuo leaving 10.18 g of crystalline residue (3R,4R)-3-amino-4-hydroxycyclopentene, m.p. 67°-75° $[\alpha]_{578}^{20}=-139°$ (c=1.0, MeOH).

Preparation 20
(1R,5R)-2,2,2-trichloroethyl-5-hydroxy-2-cyclopentene-1-carbamate

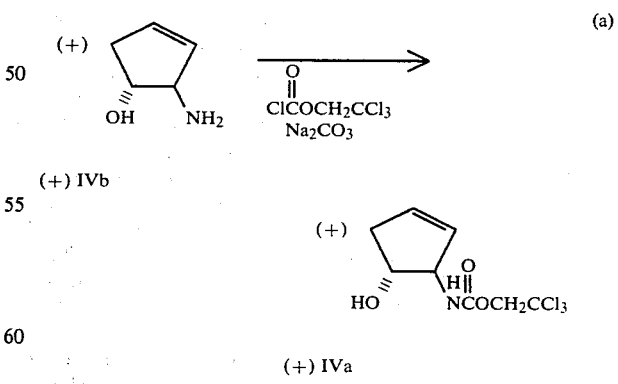

A 10.18 (103 mM) quantity of crude (3R,4R)-3-amino-4-hydroxycyclopentene (prepared as in Preparation 19, step 4) is dissolved in 75 ml of water and the mixture treated with 10.6 g (100 mM) of sodium carbonate. The mixture is then cooled in an ice bath to <10° and treated dropwise while stirring vigorously, with 24 g (110 mM) of trichloroethylchloroformate over 30 minutes. After 3 hours the reaction is filtered and the collected solid product washed thoroughly with water. On drying there is obtained 22.43 g of (1R,5R)-2,2,2-trichloroethyl-5-hydroxy-2-cyclopentene-1-carbamate as crystalline solid, m.p. 82°-84°. Recrystallization of a small sample from isopropylether-Skellysolve B gives material with a m.p. 87°-87.5° [α]−92° (C=0.14, MeOH).

TLC (silica gel 60): Rf=0.5 in (10–90) acetone-methylenechloride.

Preparation 21
(1R,5S)-2,2,2-trichloroethyl-5-(phthalimidoxy)-2-cyclopentene-1-carbamate

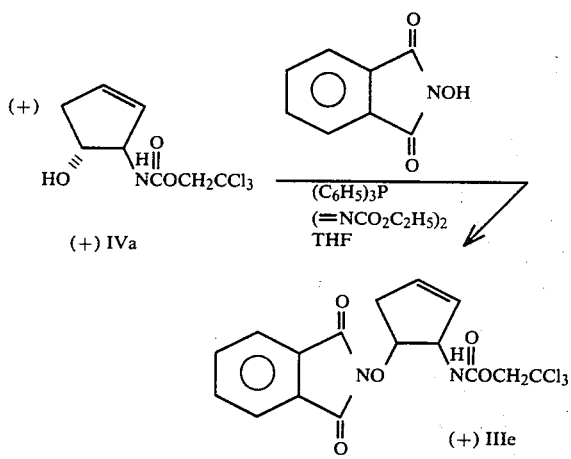

A 21 g (76.5 mM) quantity of (1R,5R)-2,2,2-trichloroethyl-5-hydroxy-2-cyclopentene-1-carbamate, a 13.76 g. (84.4 mM) quantity of N-hydroxyphthalimide, and a 22.1 g. (84.4 mM) quantity of triphenylphosphine are dissolved in 400 ml. of tetrahydrofurane dry. To the stirred solution is added dropwise over 15 minutes 16.12 g. (92.6 mM) of diethylazodicarboxylates while holding the temperature below 35° with an ice bath. The reaction is then stirred for 1 hour at 25°, after which it is concentrated in vacuo (~<25 mm. and ~30°). The residue is treated with ~100 ml. of (10–60) ethyl acetate-Skellysolve B and the precipitated triphenylphosphine oxide removed by filtration after about 15 minutes. The residue is added to the top of a 2 kg. silica gel 60 column which is eluted with 3 l. of (40–60) followed by (50—50) ethyl acetate-Skellysolve B. Three hundred ml. fractions are collected. Fractions 19–27 are found to contain pure (1R,5S)-2,2,2-trichloroethyl cis-5-(phthalimidoxy)-2-cyclopentene-1-carbamate by TLC. On concentration they yield 26.9 g. of (1R,5S)-2,2,2-trichloroethyl-5-(phthalimidoxy)-2-cyclopentene-1-carbamate crystals, 117°–118° [α]$_D$=−26° (C=0.56, MeOh).

Preparation 22
(1R,5S)-2,2,2-trichloroethyl-5-(aminooxy)-2-cyclopentene-1-carbamate

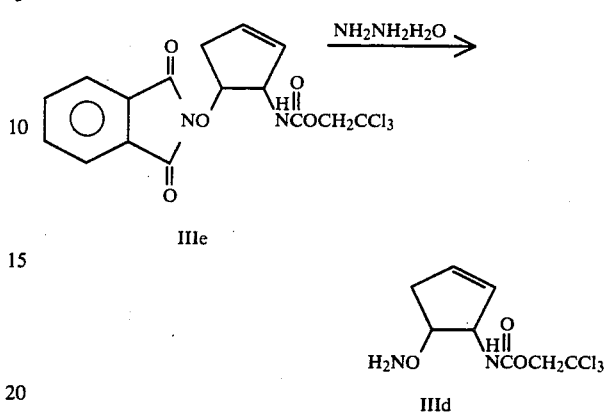

A 24.9 g. (17.67 mM) quantity of (1R,5S)-2,2,2-trichloroethyl-5-(phthalimidoxy)-2-cyclopentene-1-carbamate is dissolved in 230 ml. of tetrahydrofuran and 230 ml. of ethyl alcohol. The solution is treated with 3.3 ml. (3.4 g., 68 mM) of hydrazine hydrate. After 10 minutes a precipitate forms. After 2 hours the reaction is evaporated in vacuo (<25 mn and ~30°). The residue is triturated with methylene chloride and filtered to remove the insoluble phthalhydrazide. The filtrate is concentrated in vacuo leaving 23.3 g. of a semisolid. This material is triturated with 100 ml of ethyl acetate and filtered. The filtered solids are washed with 100 ml of methylene chloride. The combined filtrates are evaporated in vacuo leaving 18.51 g of (1R,5S)-2,2,2-trichloroethyl-5-(aminooxy)-2-cyclopentene-1-carbamate as an oil.

TLC (silica gel 60): Rf=0.41 in (5–95) methanol-benzene and Rf=0.41 in (40–60) ethyl acetate Skellysolve B.

Using the same procedure as in Preparation 23, but substituting the appropriate haloalkyl (1R,5S)-5-(phthalimidoxy)-2-cyclopentene-1-carbamate for (1R,5S)-2,2,2-trichloroethyl-5-(phthalimidoxy)-2-cyclopentene-1-carbamates there is obtained the corresponding haloalkyl-5-(aminoxy)-2-cyclopentene-1-carbamates.

Preparation 23
(1R,5S)-2,2,2-trichloroethyl-5-[[[(benzyloxy)carbonyl]amino]oxy]-2-cyclopentene-1-carbamate

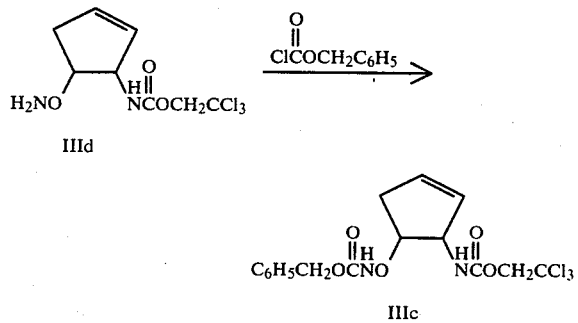

An 18.5 g. quantity of crude (1R,5S)-2,2,2-trichloroethyl-5-aminooxy-2-cyclopentene-1-carbamate prepared as in preparation 10 is dissolved in 175 ml. of pyridine and the solution cooled in an ice bath and treated with 11.6 g. (67.7 mM) of benzyloxychloroformate dissolved in 15 ml. of methylene chloride. After 1.5 hours the reaction mixture is treated with 10 ml. of water, stirred 10 minutes and the reaction mixture is poured into water and methylene chloride and treated with ammonium chloride until acidic. The methylene chloride layer is separated, dried over sodium sulfate and concentrated in vacuo leav- 22.6 g. of oil. The oil is crystallized from ether giving 5.2 g. of (1R,5S)-2,2,2-trichloroethyl[((benzyloxy)carbonyl)amino)oxy]-2-cyclopentene-1-carbamate, m.p. 89.5–90.5. A second crop of 9.17 g., m.p. 89–90 and a third crop of 1.54 g., m.p. 80–85 is obtained by crystallization of the first crop mother liquors from isopropyl ether. $[\alpha]_D = -33°$ (C=0.02, MeOH).

TLC (silica gel 60): Rf=0.73 in (40–60) ethylacetate-Skellysolve B.

Preparation 23a
(1R,5S)-2,2,2-trichloroethyl-5-[[[(t-butyloxy)carbonyl]amino]oxy]-2-cyclopentene-1-carbamate An 7.8 g. quantity of crude (1R,5S)-2,2,2-trichloroethyl-5-(aminooxy)-2-cyclopentene-1-carbamate is dissolved in 25 ml. of tetrahydrofuran and 6.15 g (25 mm) of 2-(tertbutoxycarbonyloxyimino)-2-phenylacetonitrile and the mixture stirred for 22 hours at room temperature, 20 hours at 50° C., 72 hours at room temperature and then evaporated in vacuo. The residue is chromatographed over 900 g. of silica gel eluted with (15–85) ethylacetate-toluene. Three hundred ml. fractions are collected. The product is found in fractions 10–12. Evaporation and recrystallization of the residue from Skellysolve B yields (1R,5S)-2,2,2-trichloroethyl-5-[[[(t-butyloxy)carbonyl]amino]oxy]-2-cyclopentene-1-carbamate m.p. 83°–84° C. as a white solid.

NMR (CDCl$_3$, δ): 1.45 (s,9) 2.45=2.7 (m,2), 4.3–4.9 (m, 2) 4.75 (s, 2), 5.6–6.1 (m, 3H), 7.7–7.8 (b,1).

Preparation 24
(1S,2R)-benzyl-[(2-amino-3-cyclopenten-1-yl)oxy]carbamate

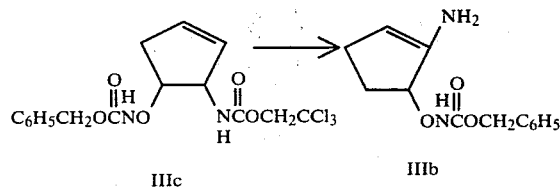

A 7.12 g. (16.8 mM) quantity of (1R,5S)-2,2,2-trichloroethyl-5-[[[(benzyloxy)carbonyl]amino]oxy]-2-cyclopentene-1-carbmate is dissolved in 75 ml. of methanol. The solution is treated with 7 g. (108 mM) of zinc dust. To this mixture is added over 10 minutes, while stirring vigorously, 2.1 ml. of methanesulfonic acid. TLC shows the reaction to be complete in less than 90 minutes. The reaction mixture is then filtered and the zinc solids washed with methanol. The filtrate and combined washings are concentrated in vacuo leaving 5.8 g of crude (1S,2R)benzyl-[(2-amino-3-cyclopenten-1-yl)oxy]carbamate which is used directly in Preparation 23.

Using the same procedure as in Preparation 24 but substituting (1R,5S)-2,2,2-trichloroethyl-5-[[[(t-butyloxy)carbonyl]amino]oxy-2-cyclopentene-1-carbamate for (1R,5S)-2,2,2-trichloroethyl-5-[[[(benzyloxy)carbonyl]amino]oxy-2-cyclopentene-1-carbamate there is obtained (1S,2R)-t-butyl-5-[(2-amino-3-cyclopentne-1-yl)oxy]carbamate.

Preparation 25
(1S,2R)-benzyl-(2-phthalimido-3-(cyclopenten-1-yl)oxy]carbamate

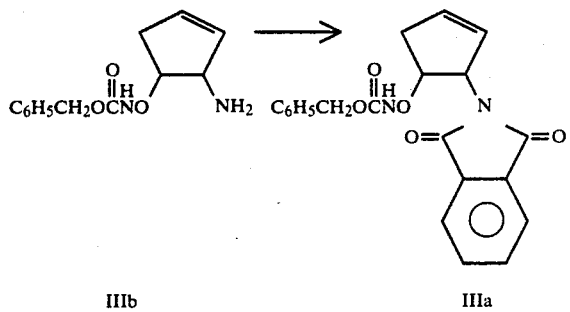

A 5.8 g. (16.8 mM) quantity of crude (1R,5R)benzyl [(2-amino-3-cyclopentene-1-yl)oxy]carbamate from Preparation 23 is dissolved in 90 ml. of tetrahydrofuran. To this is added 4.95 g (25 mM) of 2-methoxy carbonylbenzoyl chloride and 10 ml. (7.3 g., 72 mM) of triethylamine. The reaction is warmed to 50° for 72 hours at which time TLC indicates the reaction has gone to completion. The reaction is then concentrated in vacuo. The reaction is partitioned between ethyl acetate and ammonium chloride. The ethyl acetate layer is separated and washed with 5% sodium bisulfate and water and dried over magnesium sulfate. Concentration of the ethyl acetate solution in vacuo leaves 7.4 g. of crude residue. The reaction is chromatographed over 600 g. of silica gel, 60 eluted with (40–60) ethyl acetate-Skellysolve B. Fifty ml. fractions are collected. The product is found in fr 16–24 by TLC. Concentration of these fractions gives 5.2 g. (75%) of (1S,2R)-benzyl[2-phthalamido-3-(cyclopentene-yl)oxy]carbamate as a crystalline solid, m.p. 89–92 $[\alpha]_D = -143$ (C=0.7, MeOH).

TLC (silica gel 60): Rf=0.48 in (40–60) ethyl acetate-Skellysolve B.

Preparation 26
(αS,5S)-2-[(benzyloxy)carbonyl]-3-oxo-α-phthalimido-5-isoxazolidineacetic acid

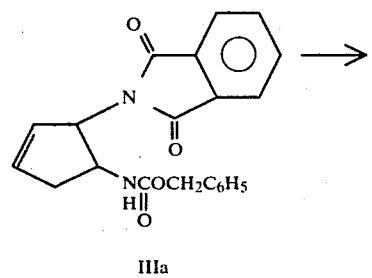

-continued

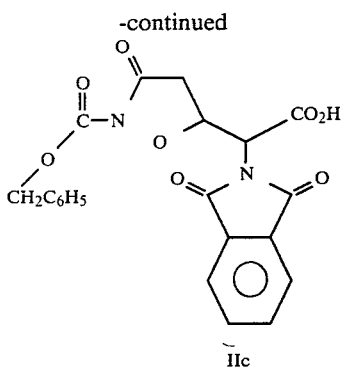

IIc

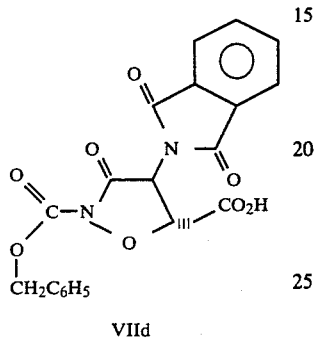

VIId

An 10.0 g (26.5 mM) quantity of (2R,3S)-benzyl-[2-phthalimido-3-cyclopenten-1-yl)oxy]carbamate IIIa is dissolved in 250 ml. of acetone and 180 ml. of water. The resultant solution is treated with 28 g. (130 mM) of sodium iodate and 100 mg. of ruthenium chloride hydrate (1–3 H₂O) in 5 ml. of water. The reaction is stirred vigorously for one hour. The reaction is then evaporated at −30 mm and <30° C. to remove acetone. The aqueous residue is partitioned between ethyl acetate and water acidified with ~10 ml of M sulfuric acid. The aqueous layer is separated and extracted two times more with ethylacetate. The combined ethyl acetate solutions are washed with saturated sodium chloride solution, dried over magnesium sulfate and concentrated in vacuo (<30 mm, <30° C.) leaving a glassy foam. The residue is added to the top of a 1 kg. of CC-4 silica gel column on 80 g. of CC-4 silica gel column on which it has been deposited by evaporation of a methylene chloride solution and eluted. Four hundred ml fractions are collected. Evaporation of fractions 16–19 yields, 7.48 g. of essentially pure (αS,5S)-2-[(benzyloxy)carbonyl]-3-oxo-α-phthalimido-5-isoxazoline acetic acid, m.p. 113°–116° [α]$_D$= −57° (C=2.0 in MeOH).

Fraction 14 yields 0.93 g. of (4S, 5S) 2-[(benzyloxy)-carbonyl]-3-oxo-4-phthalimido-5-isoxazolidine acetic acid, m.p. 160°–2° (ethyl acetate/hexane, 1:1).

A mixture of the two acids is found in Fraction 15.

Using the same procedure as in Preparation 26 but substituting (2R,3S)-t-butyl-[2-phthalimido-3-cyclopenten-1-yl)oxy]carbamate for (2R,3S)-benzyl-[2-phthalimido-3-cyclopenten-1-yl)oxy]carbamate there is obtained (α5,5S)-2-[(t-butyloxy)carbonyl]-3-oxo-α-phthalmido-5-isoxazolidine acetic acid and (4S,5S)-2-[(t-butyloxy)-carbonyl]-3-oxo-4-phthalimido-5-isoxazolidine acetic acid.

NMR (CDCl₃, δ): 1.35 (s,9), 2.7–3.0 (m, 2), 4.55–5.0 (m, 1), 5.15–5.55 (m, 1), 5.55–6.25 (m, 2), 7.2–7.4(1), 7.6–8.0 (m, 4).

Preparation 27
(α5,5S)-3-oxo-α-phthalimido-5-isoxazolidine acetic acid

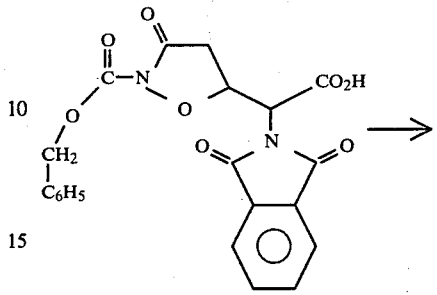

IIc

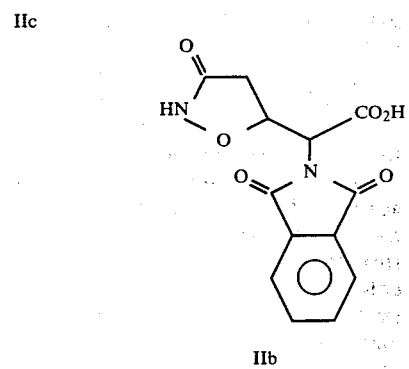

IIb

A 7.48 g. (17.6 mM) quantity of (αS,5S) 2-[(benzyloxy)carbonyl]-3-oxo-α-phthalimido-5-isoxazolidine acetic acid is dissolved in 150 ml. of ethyl acetate and 75 ml. of 95% ethanol. The solution is treated with 1.5 g. of palladium black and hydrogenated at 25° C. and 1 atmosphere of pressure. The reaction is stopped after 165 minutes, filtered, and the filtrate is evaporated in vacuo to yield 3-oxo-α-phthalimido-5-isoxazolidine acetic acid as a residue.

NMR (CD₃OD, δ): 2.92 2(partially split d, CH₂), 5.1–5.7 (m, 2), 7.85 (s, 4 ArH).

TLC (silica gel 60): Rf=0.36 in the upper phase of (9-2-5-10) ethylacetate-acetic acid cyclohexane-water. In the same system the starting material Rf=0.46 and the hydrogenated product from 33 Rf=0.54, and compound 33 Rf=0.64.

Preparation 28
(α5,5S)-3-Oxo-α-phthalimido-5-isoxazolidine acetic acid, benzhydryl ester 15b

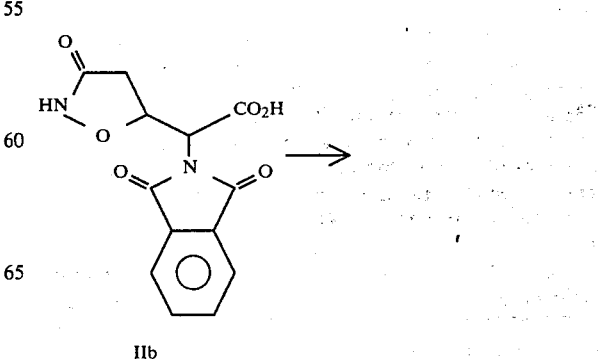

IIb

-continued

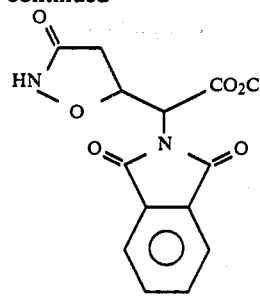

IIa

A 2.8 g (14.3 mM) quantity of benzophenone hydrazone was dissolved in 80 ml of ethyl ether. The solution is treated with 10 g of sodium sulfate, 6.02 g (28 mM) of yellow mercury oxide and 0.2 ml of a saturated potassium hydroxide solution in ethyl alcohol. The reaction is stirred 60 minutes and the resultant deep burgandy mixture filtered. The resultant solution is added directly to the reaction solution from a 8.45 mM hydrogenation in which (α5,5S)-3-oxo-α-phthalimide-5-isoxazolidine acetic acid is prepared. After one hour the reaction is treated with sufficient 3 N hydrochloric acid while stirring vigorously, to destroy the excess burgandy colored diazo compounds. The reaction mixture is then evaporated in vacuo (<30 mm and <30° C.), and chromatographed over 300 g. of CC-4 silica gel eluted with (40–60) ethyl acetate-toluene. Thirty five ml. fractions are collected. The (αS,5S) 3-oxo-α-phthalimido-5-isoxazolidineacetic acid, benzhydryl ester is found in fractions 10–14 [α]$_D$= +26° (C=0.70).

NMR (CDCl$_3$ δ): 2.75 (d, J=11.5, CH$_2$), 5.15–5.7 (m, 2), 6.93 (s, CH (C$_6$H$_5$)$_2$), 7.18 (s, C$_6$H$_5$), 7.28 (s, C$_6$H$_5$), 7.5–8.0 (m, 4, ArH).

TLC (silica gel 60): Rf=0.42 in (40–60) ethyl acetate-toluene. The isoproduct from compound VIIb has Rf=0.59 in this same system.

Preparation 29 Tricholomic Acid

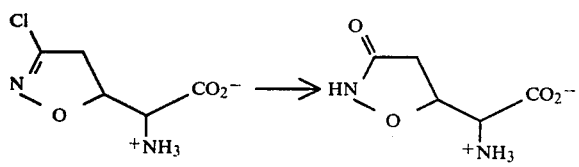

To 1.20 g. (6.75 mmole) of (αS,5S)-α-amino-3-chloro-4,5-dihydro-5-isoxazol-acetic acid (AT-125), is added 20 ml. of 2 N sodium hydroxide and stirred at 25° for 36 hours. The solution is brought to ~3.5 pH with 6 N hydrochloric acid (dropwise addition) and then stored at −10° (freezer) overnight. The crystals are collected by filtration, washed twice with cold water, and then dried giving 720 mg. of trichloromic acid. The initial filtrate is lyophilized and the resulting powder is taken up in 4 ml. of water, filtered, and washed with two 4 ml. portions of cold water, and dried yielding an extra 160 mg. of tricholomic acid (total 80% yield).

NMR (D$_2$O): 5.65–5.35 (1H, m, ring CH), 4.27 (1H, d, J=3.5 H$_3$, α-H), 3.69 (2H, d, J=9.5 H$_3$, CH$_2$).

TLC: Rf=0.31 (ninhydrin), (solvent: 60% methyl-ethyl ketone, 20% acetone, 15% water, 5% acetic acid).

C-NMR (D$_2$O): 154.6 (CONH), 79.4 (CHO), 56.8 (α-C), 36.8 (CH$_2$).

Preparation 30 Phthalyl-tricholomic acid, methyl ester

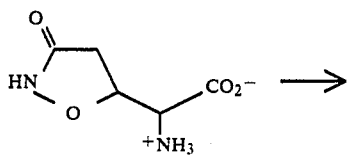

IId

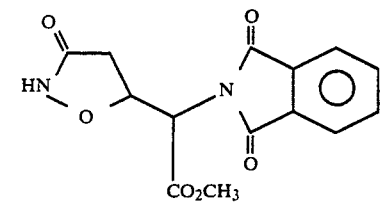

IIa$_2$

A 400 mg. (2.5 mmole) sample of tricholomic acid, 720 mg. of sodium carbonate, 6 ml. water, and 1.2 g. of N-carbethoxyphthalimide are mixed with the latter added in 3 portions over first 2 hours. After acidification to pH 3 with 3 N HCl the reaction mixture is washed with 2×25 ml. of ethyl acetate. The combined organic phases are washed with brine, dried over sodium sulfate and concentrated in vacuo. Chromatography (CC-4, 50%–75% E/H gradient) yields phthalyl-tricholomic acid.

NMR (methanol d$_4$): 7.86 (4H, s, φ), 5.65–5.0 (2H, m, CHO, α-H), 2.92 (2H, d, CH$_2$).

TLC: (AlX) Rf=0.15 (UV; yellow stain with vanillin/H$_3$PO$_4$ spray, Δ).

The product is taken up to 10 ml. of dry tetrahydrofuran and treated with etheral diazomethane. Chromatography (silica gel 75% E/H afforded 160 mg.

NMR (CDCl$_3$): 5.65–5.3 (1H, m, CHO), 5.3–5.1 (1H, m, α-H), 3.06 (2H, d, CH$_2$, PHTH unchanged.

TLC: (AlX) Rf=0.33 (50% E/H) Rf-0.15; (AT-125 derivative) Rf=0.42.

Analysis: Calc. C, 55.26; H, 3.98; N, 9.21. Found: C, 55.20; H, 4.60; N, 8.43.

Mass Spectrometry: M+ m/e 304 (3%), 272 (H+—CH$_2$OH), 244 (M+-CO$_2$CH$_3$), 219.

EXAMPLE 1

(αS,5S)-Chloro-4,5-dihydro-α-phthalimido-5-isoxazole acetic acid, benzhydryl ester

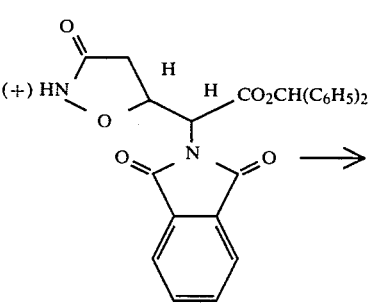

IIa$_1$

-continued

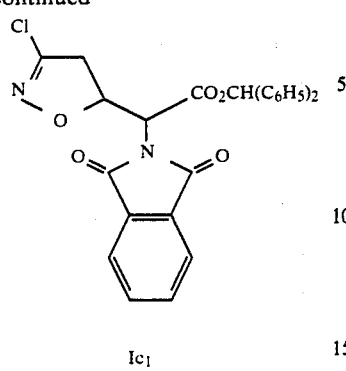

Ic₁

To 192 μl (2 mmole) of carbon tetrachloride in 25 ml of dry tetrahydrofuran under N₂ at room temperature is added 310 μl (1.9 mmole) of hexamethylphosphorous triamide dropwise over one minute. Within two minutes 590 mg. (1.3 mmole) of (αS,5S)-oxo-α-phthalimido-5-isoxazolidine acetic acid, benzhydryl ester acid in approximately 5 ml of dry THF is added rapidly. The heterogeneous solution is stirred at 45° for 48 hours. Alternatively, to 590 mg. (1.3 mmole) of (αS,5S)-oxo-α-phthalimido-5-isoxolidine in 20 ml. of dry tetrahydrofuran under N₂ at room temperature is added 610 mg. (2.6 mmole) of hexamethylphosphorous triamide dichloride (prepared by hexachloroethane in acetonitrile with hexamethylphosphorous triamide according to R. Appel and H. Schöler, Chem. Ber., 110, 2382 (1977)). The solution is refluxed for 48 hours. The reaction is taken up in 150 ml of ethyl acetate and washed with 50 ml of 0.1 N hydrochloric acid followed by brine and then dried over sodium sulfate. After concentrating in vacuo the residue is chromatographed on 50 g of silica gel with 30% ethyl acetate hexane (200 ml elution) which yields 200 mg of crude product (33% yield), 245 mg of starting material (42%). The crude product yielded (α5,5S) 3-chloro-4,5-dihydro-α-phthalimido-5-isoxazole acetic acid as needles, m.p. 178°-9° upon recrystallization from methanol.

Tlc: Rf (product)=0.70 in 35% ethyl acetate/hexane (S.M.)=0.11

(α)₂₀ (CHCl₃)+79° (589 nm) 82° (578) 94° (547) 163° (436) 256° (365)

NMR (CDCl₃): 7.80 (4H, m, PHTH), 7.32 and 7.22 (10H, s, φ), 6.95 (1H, s, φCH), 5.6 (1H, m, CHO), 5.26 (1H, d, α-H), 3.32 (2H, d, CH₂).

Analysis: Calc'd. for C₂₆H₁₉ClN₂O₅: C, 65.75; H, 4.03; N, 5.90. Found: C, 65.45; H, 4.08; N, 5.95.

Using the procedures described above but substituting the (αS,5S)-3-oxo-4,5-dihydro-4β-phthalimido-5α-isoxazole acetic acid, benzhydryl ester (VIIb) affords the (αS,5S) (resp.) 3-chloro-4,5-dihydro-4β-phthalimido-5α-isoxazole acetic acid, benzhydryl ester (VIIIc, X=Cl).

EXAMPLE 2

(αS,5S)-Chloro-4,5-dihydro-α-phthalimido-5-isoxazole acetic acid

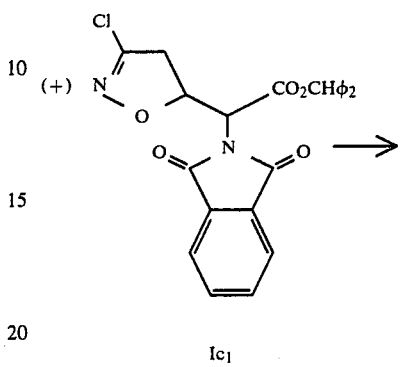

Ic₁

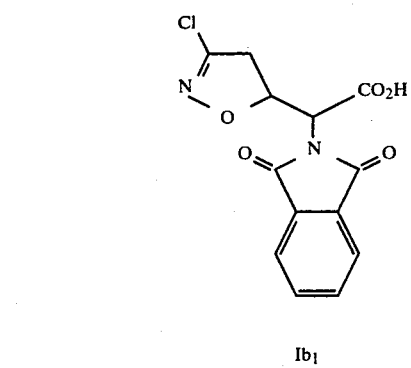

Ib₁

To 185 mg (0.4 mmole) of 3-chloro-4,5-dihydro-α-phthalimido-5-isoxazole acetic acid, benzhydryl ester in 3 ml of dry nitromethane in an ice bath under nitrogen is bubbled dry hydrogen chloride five minutes. The bath is removed and the solution stirred for one hour. After concentrating the solution in vacuo the residue is chromatographed on CC-4 silica gel (30 g) with 30% ethyl acetate/hexane to yield 115 mg of a white foam. This foam is recrystallized from 4/1 hexane/ethanol to yield (αS,5S)-3-chloro-4,5-dihydro-α-phthalimido-5-isoxazole acetic acid, a m.p. 176°-7° C. (forms a hydrate on exposure to moisture).

Tlc: Rf=0.45 (AIX)

NMR: (Acet-d₈) 7.95 (4H, s, PHTH), 5.6 (1H, m, CHO), 5.27 (1H, d, α-H), 3.57 (2H, d, CH₂).

Analysis: Calc'd for C₁₃H₉ClN₂O₅: C, 50.58; H, 2.94; N, 9.08. Found: C, 50.57; H, 3.06; N, 9.46.

Using the same procedure as described above but substituting (αS,5S)-3-chloro-4,5-dihydro-4β-phthalimido-5α-isoxazole acetic acid, benzhydryl ester (VIIIc, X=Cl) affords (αS,5S) (resp.) 3-chloro-4,5-dihydro-4β-phthalimido-5α-isoxazole acetic acid (VIIIb, X=Cl).

EXAMPLE 3

(αS,5S)-Bromo-4,5-dihydro-α-phthalimido-5-isoxazole acetic acid

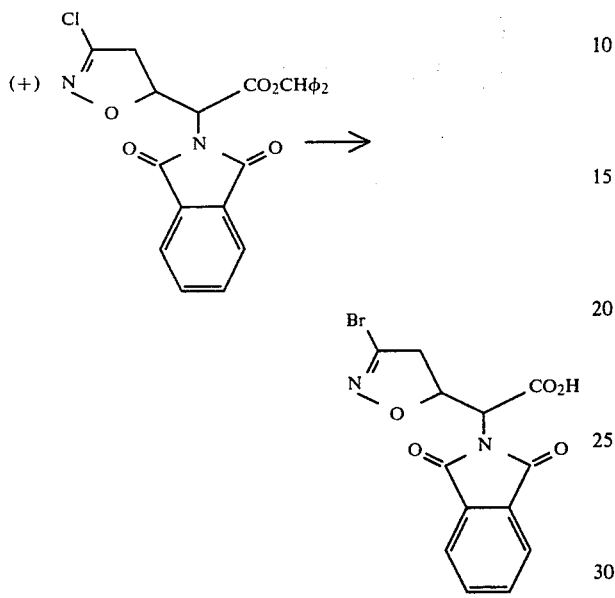

To 185 mg (0.4 mmole) of the (αS,5S)-chloro-4,5-dihydro-α-phthalimido-5-isoxazole acetic acid, benzhydryl ester in 3 ml of dry nitromethane in an ice bath under nitrogen is bubbled dry hydrogen bromide for five minutes. The bath is removed and the solution stirred for one hour. After concentrating the solution in vacuo the residue is chromatographed on CC-4 silica gel (30 g) with 30%) ethyl concentrating the solution in vacuo the residue is chromatographed on CC-4 silica gel (30 g) with 30%) ethyl acetate/hexane to yield 115 mg of a white foam. This foam is recrystallized from 4/1 hexane/ethanol to yield 3-bromo-4,5-dihydro-α-phthalimido-5-isoxazole acetic acid.

Analysis: Calc'd. for $C_{13}H_9BrN_2O_5$: C, 44.21; H, 2.57; N, 7.93. Found: C, 44.49; H, 2.64; N, 7.83. $[\alpha]_{20}$(MeOH) 67° (589 nm) 70° (578) 79° (547) 131° (436) 187° (365)

Utilizing the same procedure as in Example 3 but substituting hydrogen iodide for hydrogen bromide there is obtained 3-iodo-4,5-dihydro-α-phthalimido-5-isoxazole acetic acid.

Again utilizing the same procedure as in Example 3 but substituting hydrogen floride for hydrogen bromide there is obtained 3-fluoro-4,5-dihydro-α-phthalimido-5-isoxazole acetic acid.

EXAMPLE 4 phthalyl-(αS,5S)-α-amino-3-chloro-4,5-dihydro-5-isoxazol-acetic acid methyl ester from phthalyltricholomic acid methyl ester

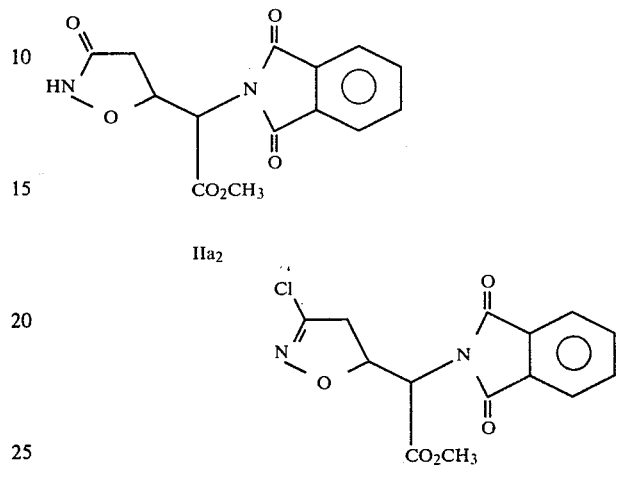

To 60 mg. (0.2 mmole) of tricholomic acid ester phthalimide in 1 ml. of dry tetrahydrofuran at room temperature under $N_2$ is added 25 μl of carbon tetrachloride followed by 30 μl of hexamethylphosphorous triamide. After 16 hours another 10 μl of carbon tetrachloride and 10 μl of phosphine were added. The solution was worked up after a total reaction time of 36 hours with ethyl acetate/water. The products are chromatographed on 5 g. silica gel (50% E/H) to recover 35 mg. of phthalyl-(α5,5S)-α-amino-3-chloro-4,5-dihydro-5-isoxazol-acetic acid methyl ester.

NMR: (CDCl₃) identical to AT-125-PHTH methyl ester, prepared from natural (+) AT-125 followed by Preparation 30.

TLC: identical to AT-125-PHTH methyl ester (UV and staining identical).

EXAMPLE 5

(αS,5S)-α-amino-3-chloro-4,5-dihydro-5-isoxazole acetic acid or AT-125

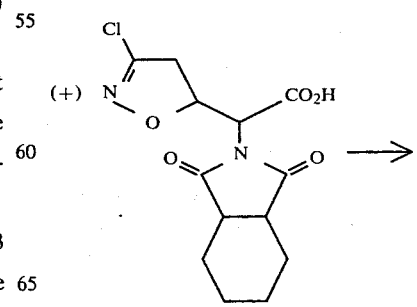

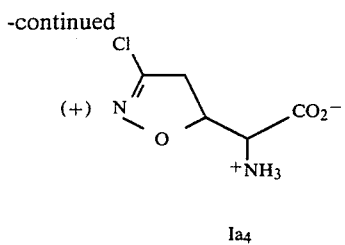

Ia₄

To 710 mg (2.3 mmole) of 3-chloro-4,5-dihydro-α-phthalimido-5-isoxazole acetic acid in 15 ml of water is added 260 μl of hydrazine hydrate and the solution stirred at 50° for 7 hours. After cooling, the solution is adjusted to pH 5.5 with acetic acid (80 μl), filtered, and the precipitate washed with 13 ml water. The filtrate is diluted with 200 ml of 2-butanol and allowed to crystallized in the refrigerator for 18 hours. Filtration yielded 240 mg of (αS,5S)-α-amino-3-chloro-4,5-dihydro-5-isoxazole acetic acid; concentrating the mother liquors approximately 15% afforded 50 mg of a second crop of (αS,5S)-α-amino-3-chloro-4,5-dihydro-5-isoxazole acetic acid (71%).

Tlc: Rf 0.40 (60/20/15/5; MEK/ACet/H₂O/AcOH).

Nmr: (D₂O) 5.2 (1H, m, C$\underline{H}$O), 4.17 (1H, d, α-H), 3.61 (2H, d, CH₂).

Using the same procedure as described above but substituting DL- or D-3-chloro-4,5-dihydro-4β-phthalimido-5α-isoxazole acetic acid (VIIIb, X=Cl) affords DL- or D-(resp.)-3-chloro-4,5-dihydro-4β-amino-5α-isoxazole acetic acid (VIIIa). A similar substitution of IIb for Ib affords tricholomic acid.

Analysis: Calc'd. for C₅H₉ClN₂O₃: C, 33.63; H, 3.95; N, 15.69; Cl, 19.86.

CD: $\theta_{216}{}^{max}=13,300$ Found: C, 33.60; H, 4.11; N, 16.15; Cl, 19.63.

EXAMPLE 6

(αS,5S)-α-amino-3-bromo-4,5-dihydro-5-isoxazole acetic acid

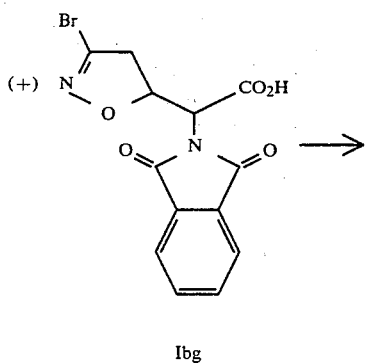

Ibg

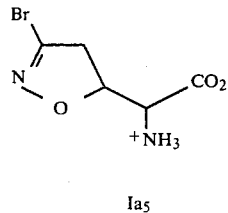

Ia₅

To 710 mg (2.3 mmole) of 3-bromo-4,5-dihydro-α-phthalimido-5-isoxazole acetic acid in 15 ml of water is added 260 μl of hydrazine hydrate and the solution stirred at 50° for 7 hours. After cooling, the solution is adjusted to pH 5.5 with acetic acid (80 μl), filtered, and the precipitate washed with 13 ml water. The filtrate is diluted with 200 ml of 2-butanol and allowed to crystallized in the refrigerator for 18 hours. Filtration yielded 240 mg of (αS,5S)-α-amino-3-bromo-4,5-dihydro-5-isoxazole acetic acid; concentrating the mother liquors approximately 15% afforded 50 mg of a second crop of (αS,5S)-α-amino-3-bromo-4,5-dihydro-5-isoxazole acetic acid (71%).

The tlc and nmer were indistinguishabel from the chloro-analog. The UV spectrum exhibited the same extinction but at 214 nm.

CD: $\theta_{213}{}^{max}=11,250$

Analysis: Calc'd for C₅H₇BrN₂O₃: C, 26.92; H, 3.16; N, 12.56; Br, 15.73. Found: C, 26.63; H, 3.33; N, 12.60; Br, 15.58.

(Br determined from Cl coulometric assay)

MS: on disilyl compound indicates M⁺-15 at 352 and 354 m/e.

EXAMPLE 7

Direct conversion of Tricholomic Acid to AT-125

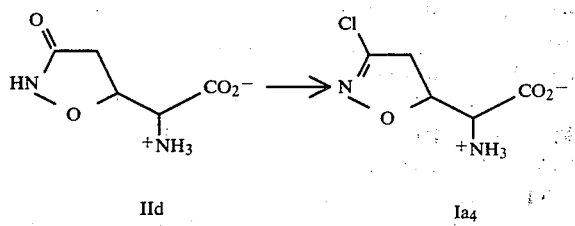

IId           Ia₄

To 140 mg. of tricholomic acid in 3 ml. POCl₃ under N₂ at room temperature was added 160 μl of purified diethylaniline. The mixture was placed in a 100° bath for 5 minutes. The POCl₃ was removed in vacuo. The resultant solid was treated with 2 ml. H₂O and stirred for 10 minutes while neutralizing with concentrated NH₄OH. After lyophilization the material was applied to a 10 g. silica gel column and eluted with 85% EtOAc/5% H₂O/10% acetic acid. A dark band with TLC mobility similar to AT-125 was recovered. The material was bio-assayed against B. subtilis (syn.) and found to exhibit a minimum of 2% yield (assuming that starting tricholomic acid is 100% pure and knowing the bioactivity of tricholomic acid).

EXAMPLE 8

(αS,5S)-3-methoxy-4,5-dihydro-α-phthalimido-5-isoxazole acetic acid, benzhydryl ester

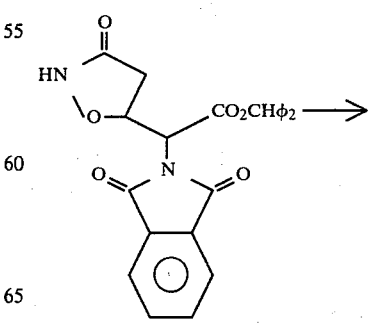

IIa

-continued

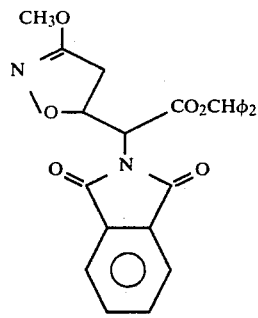

Ic (X = OCH₃)

To 90 mg. (0.2 mmole) of 3-oxo-α-phthalimido 5-isoxazolidine acetic acid, benzhydryl ester (IIa) in 5 ml of methylene chloride is added a 50% molar excess of a standard etheral diazomethane solution. A 5 μl. amount of βF₃.Et₂O is added and, after 30 minutes, the reaction is concentrated and the residue chromatographed on preparative TLC (AIX eluent) to yield (45 mg) of 3-methoxy-4,5-dihydro-α-phthalimido-5-isoxazole acetic acid, benzhydryl ester.

NMR (CDCl₃): 7.80 (m, 4H), 7.32 and 7.22 (s, 10H, Ph), 6.96 (s, Ph₂CH), 5.1–5.8 (m, 2H), 3.75 (s, CH₃O), 3.07 (d, J=7.5 Hz, 2H)

TLC (AIX)=Rf=0.60

A second product is produced (35 mg) having the structure

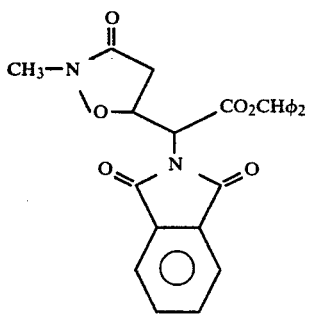

IId

NMR (CDCl₃): 7.82 (m, 4H), 7.32 and 7.22 (s, 10H), 6.97 (s, 1H), 5.1–5.9 (m, 2H), 3.10 (s, NCH₃), 2.81 (m, 2H)

TLC A IX): Rf=0.40

EXAMPLE 9

Phthalyl-(αS,5S)-α-amino-3-chloro-4,5-dihydro-5-isoxazoleacetic acid, methyl ester

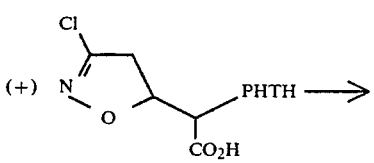

-continued

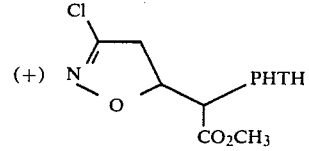

To 110 mg. (0.35 mM) of phthalyl-(αS,5S)-α-amino-3-chloro-4,5-dihydro-5-isoxazol acetic acid in 3 ml. of ether is added ethereal diazomethane until gas evolution ceased and the yellow color persists. Concentration and chromatography on 15 g of silica gel (40% ethylacetate/hexane to yields 110 mg of phthalyl-(αS,5S)-α-amino-3-chloro-4,5-dihydro-5-isoxazoleacetic acid, methyl ester as an oil (95%).

NMR (CDCl₃): 7.87 (4H, m, φ), 5.6 (1H, m, CHO), 5.22 (1H, d, J=6 Hz, α-H), 3.78 (3H, s, CH₃), 3.40 (2H, d, J=9 Hz, CH₂).

TLC: (AIX) RF=0.50, (85% E/H) Rf=0.70. ¹³C NMR: (CDCl₃) 167.5 (CO₂), 167.1 (CON), 149.9 (C-Cl), 134.7, 131.5, 124.0 (φ), 80.2 (CHO), 53.1 (CH₃), 52.9 (α-C), 41.5 (CH₂).

Analysis: Calc'd C, 52.10; H, 3.44; N, 8.68. Found: C, 52.58; H, 3.67; N, 8.39.

Mass spectrometry: no M⁺ m/e 322, 291 (M⁺-OCH₃), 287 (M⁺-Cl), 263 (M⁺-CO₂CH₃), 219 (62%, PHTH-COCHO₂CH₃).

EXAMPLE 10

3-Chloro-α-[[(9H-fluoren-9-ylmethoxy)carbonyl]amino]-4,5-dihydro-5-isoxazole acetic acid To 178 mg. of AT-125 in 4 ml. of water is added 300 mg. of sodium bicarbonate. After cooling the mixture to 0°–5° C., 300 mg. of 9-hydroxymethyl fluorenylcarbonyl chloride is added and it is stirred for two hours and allowed to stand overnight at room temperature. The resulting semi solid is taken up in ethyl acetate and 1 N hydrochloric acid is added until a pH of 3 is attained. The organic phase is separated, dried over sodium sulfate, concentrated and chromatographed on 20 g. of CC-4 silica gel employing 40% ethyl acetate/Hexane. Those fractions containing the desired product are evaporated and the residue recrystallized from ethyl acetate to yield 3-chloro-α-[[(9H-fluoren-9-yl-methoxy)carbonyl]amino]-4,5-dihydro-5-isoxazole acetic acid, m.p. 182°–183° C. The NMR fits the desired structure.

EXAMPLE 11

Phthalyl-(αS,5S)-α-amino-3-chloro-4,5-dihydro-5-isoxazole acetic acid, p-methoxybenzyl ester

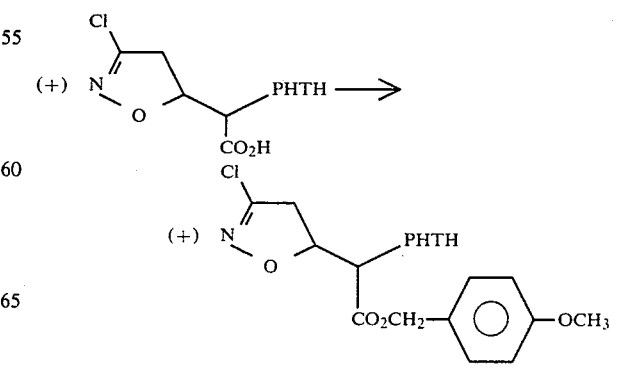

To 33 mg (0.1 mmole) of phthalyl-(αS,5S)-α-amino-3-chloro-4,5-dihydro-5-isoxazole acetic acid in 2 ml of dry acetonitrile is added 50 μl of diisopropylethylamine followed by 30 mg of 4-methoxybenzyl bromide. After stirring at room temperature under nitrogen for 6 hours, the reaction solution is taken up in ethyl acetate and 0.5 hydrochloric acid. The organic phase is separated, dried over sodium sulfate, and concentrated in vacuo. The resulting residue is chromatographed on preparative-layer silica gel plates with 40% ethyl acetate/hexane eluent. The desired band is removed, yielding 35 mg (85%) of phthalyl-(αS,5S)-α-amino-3-chloro-4,5-dihydro-5-isoxazole acetic acid, p-methoxybenzyl ester.

NMR (CDCl$_3$): 7.84 (4H, m, PHTH), 7.26 and 6.83 (4H, A$_2$B$_2$, φ), 5.6 (1H, m, CHO), 5.2 (1H, d, J=6 Hz, α-H), 4.64 (2H, s), 3.78 (3H, s), 3.38 (2H, d, J=9 Hz).

We claim:

1. Racemic mixtures and optically active isomers of compounds having the formula

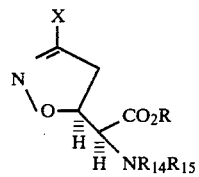

wherein R is selected from the group consisting of hydrogen, alkyl of from 1 to 8 carbon atoms, inclusive, halogenated alkyl of from 1 to 3 halogen atoms, and 1 to 5 carbon atoms, inclusive, aralkyl of from 7 to 20 carbon atoms, inclusive, and substituted aralkyl of from 7 to 20 carbon atoms, inclusive; X is selected from the group consisting of bromine, chlorine, fluorine and iodine, —OR$_1$, —SR$_1$, and —NR'R'' wherein R$_1$ is selected from the group consisting of alkyl of from 1 to 12 carbon atoms, inclusive, aryl of from 6 to 20 carbon atoms, inclusive, aralkyl of from 7 to 20 carbon atoms, inclusive; R' and R'' are the same or different and are selected from the group consisting of hydrogen and alkyl of from 1 to 8 carbon atoms, inclusive, R$_{14}$ and R$_{15}$ are selected from the group consisting of hydrogen,

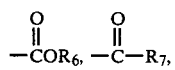

inclusive, or when taken together with the nitrogen atom form the group

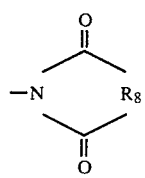

wherein R$_6$ is alkyl of from 1 to 8 carbon atoms, inclusive, halogenated alkyl of from 1 to 5 carbon atoms, inclusive, and 1 to 3 halogen atoms, inclusive, aralkyl of from 7 to 20 carbon atoms, inclusive, and substituted aralkyl of from 7 to 20 carbon atoms, inclusive, R$_7$ is selected from the group consisting of alkyl of from 1 to 12 carbon atoms, inclusive, aryl of from 6 to 20 carbon atoms, inclusive, aralkyl of from 7 to 20 carbon atoms, inclusive, substituted aralkyl of from 7 to 20 carbon atoms, inclusive, and R$_8$ is selected from the group consisting of (a)

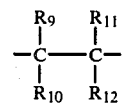

where R$_9$, R$_{10}$, R$_{11}$ and R$_{12}$ are selected from the group consisting of hydrogen and alkyl of from 1 to 5 carbon atoms, inclusive, (b)

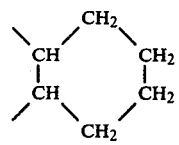

(c) orthointerphenylene, and (d) substituted orthointerphenylene, with the proviso that when R, R$_{14}$ and R$_{15}$ are all hydrogen, X cannot be chlorine, and with the further proviso that when X is chlorine and R is either hydrogen or lower alkyl of from 1 to 8 carbon atoms, inclusive, neither R$_{14}$ nor R$_{15}$ can be alkoxycarbonyl nor can R$_{14}$ and R$_{15}$ together with the nitrogen atom be the group

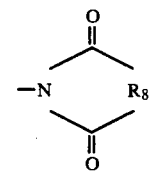

wherein R$_8$ is defined as above.

2. The racemic mixtures and optically active isomers of the compounds of claims 1, wherein X is selected from the group consisting of bromine, chlorine, fluorine and iodine.

3. The racemic mixtures and optically active isomers of the compounds of claims 1, wherein X is —OR$_1$.

4. The racemic mixtures and optically active isomers of the compounds of claims 1, wherein X is —SR$_1$.

5. The racemic mixtures and optically active isomers of the compounds of claims 1, wherein X is —NR'R'', wherein R' and R'' are the same or different and are selected from the group consisting of hydrogen and alkyl of from 1 to 8 carbon atoms, inclusive.

6. Compounds according to claim 2 wherein R$_{14}$ and R$_{15}$ are hydrogen.

7. Compounds according to claim 2 wherein R$_{14}$ and R$_{15}$ when taken together with the nitrogen atom form the group

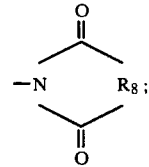

wherein R$_8$ is selected from (a) the group consisting of

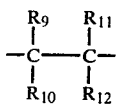

where $R_9$, $R_{10}$, $R_{11}$ and $R_{12}$ are selected from the group consisting of hydrogen and alkyl of from 1 to 5 carbon atoms, inclusive, (b)

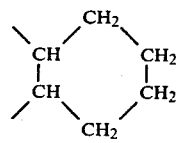

(c) orthointerphenylene, and (d) substituted orthointerphenylene.

8. Compounds according to claim 3 wherein $R_{14}$ and $R_{15}$ are both hydrogen.

9. Compounds according to claim 3 wherein $R_{14}$ and $R_{15}$ when taken together with the nitrogen atom form the group

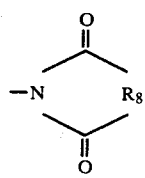

wherein $R_8$ is selected from (a) the group consisting of

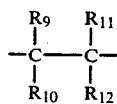

where $R_9$, $R_{10}$, $R_{11}$ and $R_{12}$ are selected from the group consisting of hydrogen and alkyl of from 1 to 5 carbon atoms, inclusive, (b)

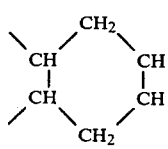

(c) orthointerphenylene, and (d) substituted orthointerphenylene.

10. Compounds according to claim 4 wherein $R_{14}$ and $R_{15}$ are both hydrogen.

11. Compounds according to claim 4 wherein $R_{14}$ and $R_{15}$ when taken together with the nitrogen atom form the group

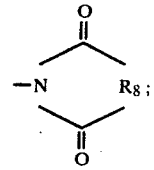

wherein $R_8$ is selected from (a) the group consisting of

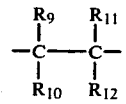

wherein $R_9$, $R_{10}$, $R_{11}$ and $R_{12}$ are selected from the group consisting of hydrogen and alkyl of from 1 to 5 carbon atoms, inclusive, (b)

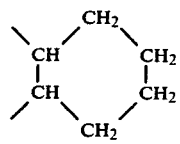

(c) orthointerphenylene, and (d) substituted orthointerphenylene.

12. Compounds according to claim 5 wherein $R_{14}$ and $R_{15}$ are both hydrogen.

13. Compounds according to claim 5 wherein $R_{14}$ and $R_{15}$ when taken together with the nitrogen atom form the group

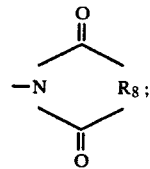

wherein $R_8$ is selected from (a) the group consisting of

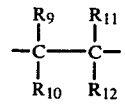

where $R_9$, $R_{10}$, $R_{11}$ and $R_{12}$ are selected from the group consisting of hydrogen and alkyl of from 1 to 5 carbon atoms, inclusive, (b)

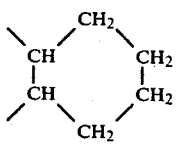

(c) orthointerphenylene, and (d) substituted orthointerphenylene.

14. A compound according to claim 9 wherein R is benzhydryl, $R_8$ is orthointerphenylene, and x is methoxy so that the specific embodiment is ($\alpha$S,5S)-3- methoxy-4,5-dihydro-α-phthalimido-5-isoxazole acetic acid, bezhydryl ester.

15. A compound according to claim 6, wherein R is p-methoxybenzyl, $R_{14}$ and $R_{15}$ are both hydrogen and X is chlorine, so that the specific embodiment is p-methoxybenzyl-(αS,5S)-α-amino-3-chloro-4,5-dihydro-5-isoxazole acetate.

16. A compound according to claim 7 wherein R is p-methoxybenzyl, $R_8$ is orthointerphenylene and X is chlorine so that the specific embodiment is phthalyl-(αS,5S)-α-amino-3-chloro-4,5-dihydro-5-isoxazolacetic acid p-methoxybenzyl ester.

17. A compound according to claim 7 wherein R is benzhydryl, $R_8$ is orthointerphenylene, and X is chlorine so that the specific embodiment is (αS,5S)-3-chloro-4,5-dihydro-α-phthalimido-5-isoxazole acetic acid, benzhydryl ester.

18. A compound according to claim 7 wherein R is hydrogen, $R_8$ is orthointerphenylene and X is bromine so that the specific embodiment is (αS,5S)-3-bromo-4,5-dihydro-α-phthalimido-5-isoxazole acetic acid.

19. A compound according to claim 7 wherein R is benzhydryl, $R_8$ is orthophenylene and X is methoxy, so that the specific embodiment is (αS,5S)-3-methoxy-4,5-dihydro-α-phthalimido-5-isoxazole-acetic acid, benzhydryl ester.

20. A compound according to claim 6 wherein R is hydrogen and X is bromine so that the specific embodiment is (αS,5S)-α-amino-3-bromo-4,5-dihydro-5-isoxazole acetic acid.

21. A compound according to claim 1 wherein R and $R_{14}$ are both hydrogen, $R_{15}$ is fluoroenylmethoxycarbonyl and X is chlorine, so that the specific embodiment is 3-chloro-α-[[(9H-fluorenyl-2-ylmethoxy)-carbonyl]amino]-4,5-dihydro-5-isoxazole acetic acid.

* * * * *

UNITED STATES PATENT OFFICE
CERTIFICATE OF CORRECTION

Patent No. 4,256,898   Dated March 17, 1981

Inventor(s) Robert C. Kelly and Wendell Wierenga

It is certified that error appears in the above-identified patent and that said Letters Patent are hereby corrected as shown below:

Column 14, line 29: "product IIIa" should read: -- product IIb --.
Column 17, line 47: "chloine" should read: -- chlorine --.
Column 20, lines 60-61: "to yield left 2.64 g" should read: -- to yield 2.64 g --.
Column 26, line 40: "IV6" should read: -- IVb --.
Column 29, line 11: "penetene-1" should read: -- pentene-1 --.
Column 29, Formula IVe: "NCOCH$_2$C$_8$H$_5$" should read: -- NCOCH$_2$C$_6$H$_5$ --.
Column 29, continuing Formula IVe: "(C$_8$H$_5$)$_3$P" should read: -- (C$_6$H$_5$)$_3$P --.
Column 31, line 53: "(CDC13)" should read: -- (CDCl$_3$) --.
Column 33, line 48: "solved" should read: -- dissolved --.
Column 38, line 19: "(,2H)" should read: -- (s, 2H) --.
Column 38, line 23: "isotrichlomic" should read: -- isotricholomic --.
Column 38, line 24: "isotrichlomic" should read: -- isotricholomic --.
Column 39, lines 35-40 (Formula IVb): " 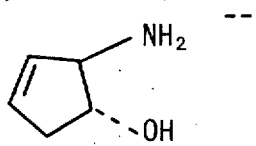 " should read: -- 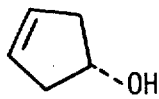 --

Column 40, line 31: "mloof" should read: -- ml of --.
Column 40, line 33: "1 hours" should read: -- 1 hour --.
Column 44, line 4: "cyclopentne" should read: -- cyclopentene --.
Column 45, line 36: "-30 mm" should read: -- <30 mm --.

UNITED STATES PATENT OFFICE
CERTIFICATE OF CORRECTION

Patent No. 4,256,898　　　　　　　　　Dated　March 17, 1981

Inventor(s) Robert C. Kelly and Wendell Wierenga

It is certified that error appears in the above-identified patent and that said Letters Patent are hereby corrected as shown below:

Column 47, lines 33-34: "fr actions" should read: -- fractions --.

Column 47, line 58: "trichloromic acid" should read: -- tricholomic acid --.

Column 48, lines 55-65 (Formula IIa$_1$): " 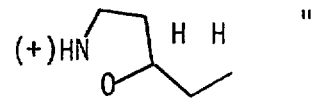 " should read: -- 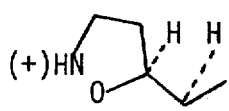 --

Column 50, line 55: "(Acet-d$_8$)" should read: -- (Acet-d$_6$) --.

Column 53, lines 18-19: "crystallized" should read: -- crustallize --.

Column 53, line 24: "/ACet/-" should read: -- /Acet/ --.

Column 54, lines 4-5: "crystallized" should read: -- crystallize --.

Column 54, line 11: "nmer were indistinguishabel" should read: -- nmr were indistinguishable --.

Column 56, line 31: "-9-ylmethoxy)" should read" -- -9-yl-methoxy) --.

UNITED STATES PATENT OFFICE
CERTIFICATE OF CORRECTION

Patent No. 4,256,898     Dated March 17, 1981

Inventor(s) Robert C. Kelly and Wendell Wierenga

It is certified that error appears in the above-identified patent and that said Letters Patent are hereby corrected as shown below:

Column 58, Claim 2, line 40: "claims 1" should read: -- claim 1 --.
Column 58, Claim 3, line 44: "claims 1" should read: -- claim 1 --.
Column 58, Claim 4, line 46: "claims 1" should read: -- claim 1 --.
Column 58, Claim 5, line 48: "claims 1" should read: -- claim 1 --.
Column 62, Claim 21, line 17: "-2-ylmethoxy)-" should read:
-- -2-yl-methoxy)- --.

Signed and Sealed this

Twenty-second Day of March 1983

[SEAL]

Attest:

GERALD J. MOSSINGHOFF

Attesting Officer     Commissioner of Patents and Trademarks